United States Patent [19]

Mookherjee et al.

[11] Patent Number: 5,369,978
[45] Date of Patent: Dec. 6, 1994

[54] AROMA EMISSION ANALYSIS SYSTEM USING A MULTIPLICITY OF INDIVIDUAL ENCLOSURES

[75] Inventors: Braja D. Mookherjee, Holmdel; Richard A. Wilson, Westfield; Robert W. Trenkle, Brielle; Michael J. Zampino, Roselle Park; Edward S. Everett, Spring Lake Heights, all of N.J.

[73] Assignee: International Flavors & Fragrances Inc., New York, N.Y.

[21] Appl. No.: 194,261

[22] Filed: Feb. 10, 1994

Related U.S. Application Data

[63] Continuation-in-part of Ser. No. 92,463, Jul. 16, 1993, which is a continuation-in-part of Ser. No. 988,337, Dec. 9, 1992, Pat. No. 5,269,169.

[51] Int. Cl.$^5$ ............... G01N 30/86; G01N 33/48; A61K 7/46
[52] U.S. Cl. ............... 73/23.34; 73/23.42; 47/69; 512/5; 512/2; 512/3
[58] Field of Search ............... 73/23.34, 23.43; 47/69, 47/1.01

[56] References Cited

U.S. PATENT DOCUMENTS

| D. 338,398 | 8/1993 | Mookherjee | D9/305 |
|---|---|---|---|
| 2,837,912 | 6/1958 | Moncrieff | 73/23.34 |
| 5,136,805 | 8/1992 | Mookherjee | 47/69 |
| 5,183,510 | 2/1993 | Kimura | 118/719 |
| 5,263,359 | 11/1993 | Mookherjee et al. | 73/23.34 |
| 5,269,169 | 12/1993 | Trenkle et al. | 73/23.34 |

OTHER PUBLICATIONS

Chemical Abstracts 119:164485p (Sep. 20, 1993).
Chemical Abstracts 119:115286j (1988).
Chemical Abstracts 108:155704e (1988).
Chemical Abstracts 117:263861y (1992).
Chemical Abstracts 117:198199x.
Chemical Abstracts 102:208465n (1985).
Chemical Abstracts 101:96725t.
Chemical Abstracts 98:155121p (1983).
Chemical Abstracts 119:124798m (1993).
Ciccioli, et al, Comm. Eur. Communities [Rep.] Eur 1984, Eur 9436, Phys.-Chem. Behav. Atmos. Pollut. 62–73 (abstracted at Chem. Abstracts vol. 102:208465n (1985).
Johansson, et al, J. Geophys. Res., [Atmos.] 1993, 98(D3), 5121-33 (abstracted at Chem. Abstracts vol. 119:164485p (Sep. 20, 1993).
Adams, R. P., Mod. Methods Plant Anal. New Ser., 1991, 12 (Essent. Oils Waxes), 131–57 (abstracted at Chem. Abstracts vol. 117:198199x).
Das, T. N., Atmos. Environ. Part A 1992, 26A(15), 3853–7 (abstracted at Chem. Abstracts vol. 117:263861y (1992).

(List continued on next page.)

Primary Examiner—Hezron E. Williams
Assistant Examiner—J. David Wiggins
Attorney, Agent, or Firm—Arthur L. Liberman

[57] ABSTRACT

Described is a process for qualitatively and quantitatively substantially continuously analyzing the aroma emitted and rates of emission of the aroma components thereof from two or more different varieties and/or species of living leaves, living fruits, living trees or living flowers at a given point in time or over a given time period using a multiplicity of enclosures to each contain one or more living leaves, living fruits, living flowers or cover surface portions of living trees or living fruits (one or more per enclosure) and having a single aroma trapping means communicating with all of the enclosures, and apparatus for carrying out such process. Also described is a process for preparing one or more perfume compositions comprising the steps of carrying out the aforementioned analysis or analyses and then, using the results of such analysis or analyses, providing and admixing at least the major components found in the analysis or analyses; apparatus for carrying out such process and perfume compositions prepared using such apparatus and process.

15 Claims, 23 Drawing Sheets

OTHER PUBLICATIONS

Mookherjee, et al, (I), Aersol Age, May 1989, pp. 21–23, 44 and 45, entitled "IFF's 'Living Flowers' Technique".

Mookherjee et al, (II), J. Ess. Oil Res. No. 2, pp. 85–90 (Mar./Apr. 1989), title "Live Vs. Dead, Part No. II, A Comparative Analysis Of The Headspace Volatiles Of Some Important Fragrance And Flavor Raw Materials".

Lawrence, et al, Proceedings Of The Tenth International Congress Of Essential Oils, Fragrances And Flavors, Washington, D.C., 16–20, Nov. 1986, published by Elsevier, 1988, Article at p. 415, "Fruits And Flowers:Live Versus Dead–Whish Do We Want"? by Mookherjee, et al.

Teranishi, et al, ACS Symposium Series 388, "Flavor Chemistry/Trends And Developments"; 195th National Meeting Of The American Chemical Society, Toronto, Canada, Jun. 5–11, 1989, Article at p. 176 (Chapter 14): Mookherjee, et al, New Dimensions In Flavor Research/Herbs And Spices.

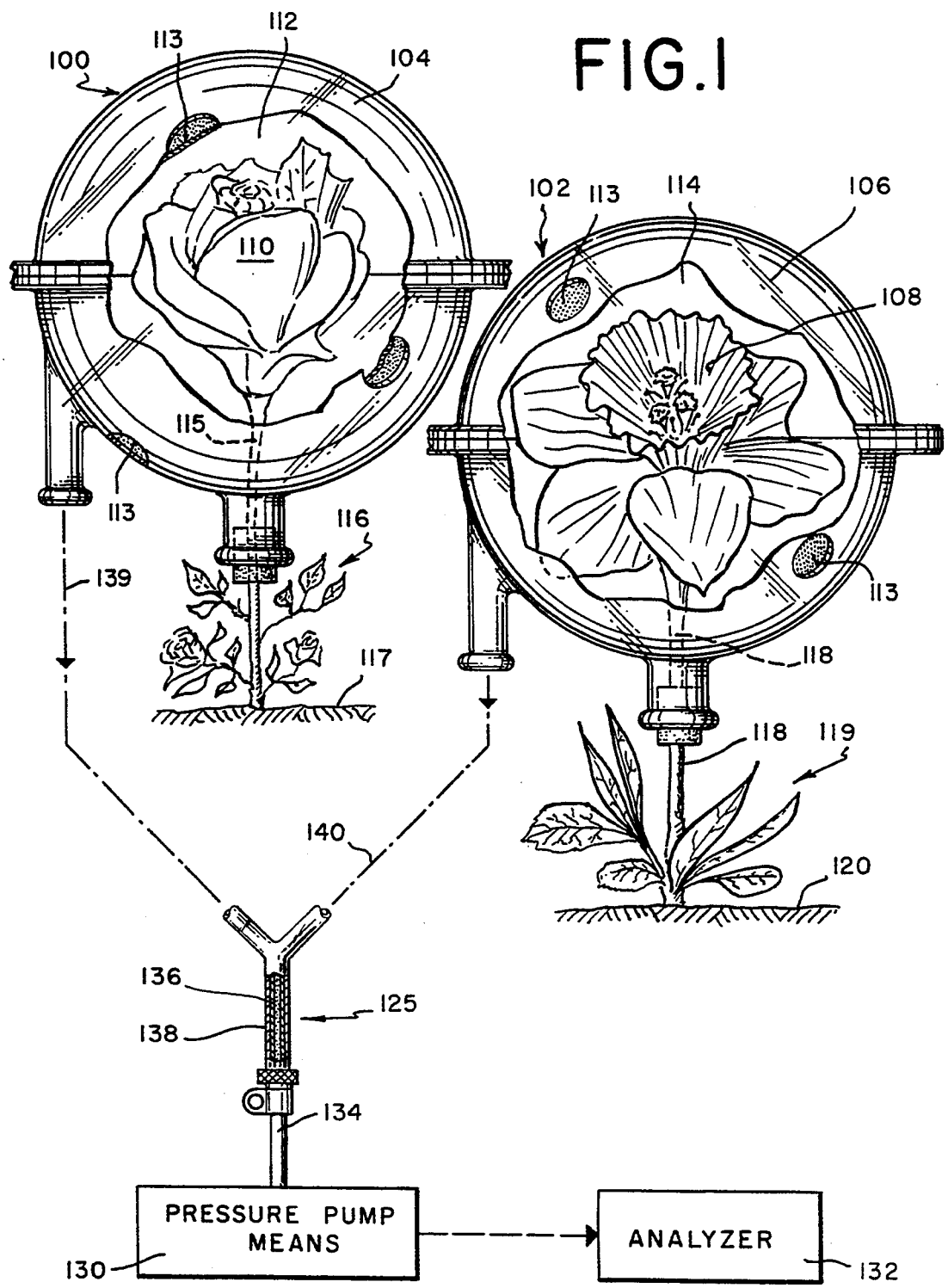

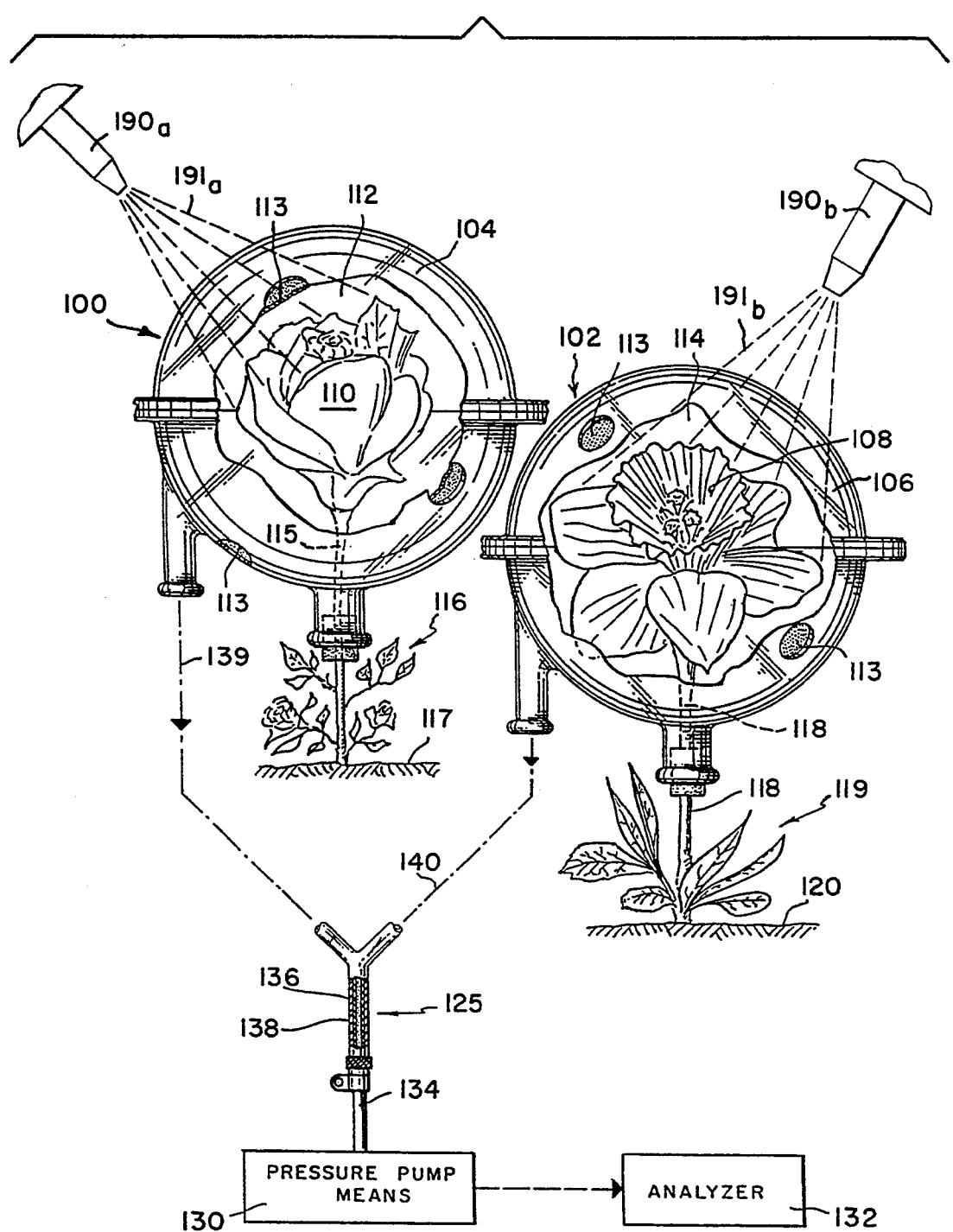
FIG.I-A

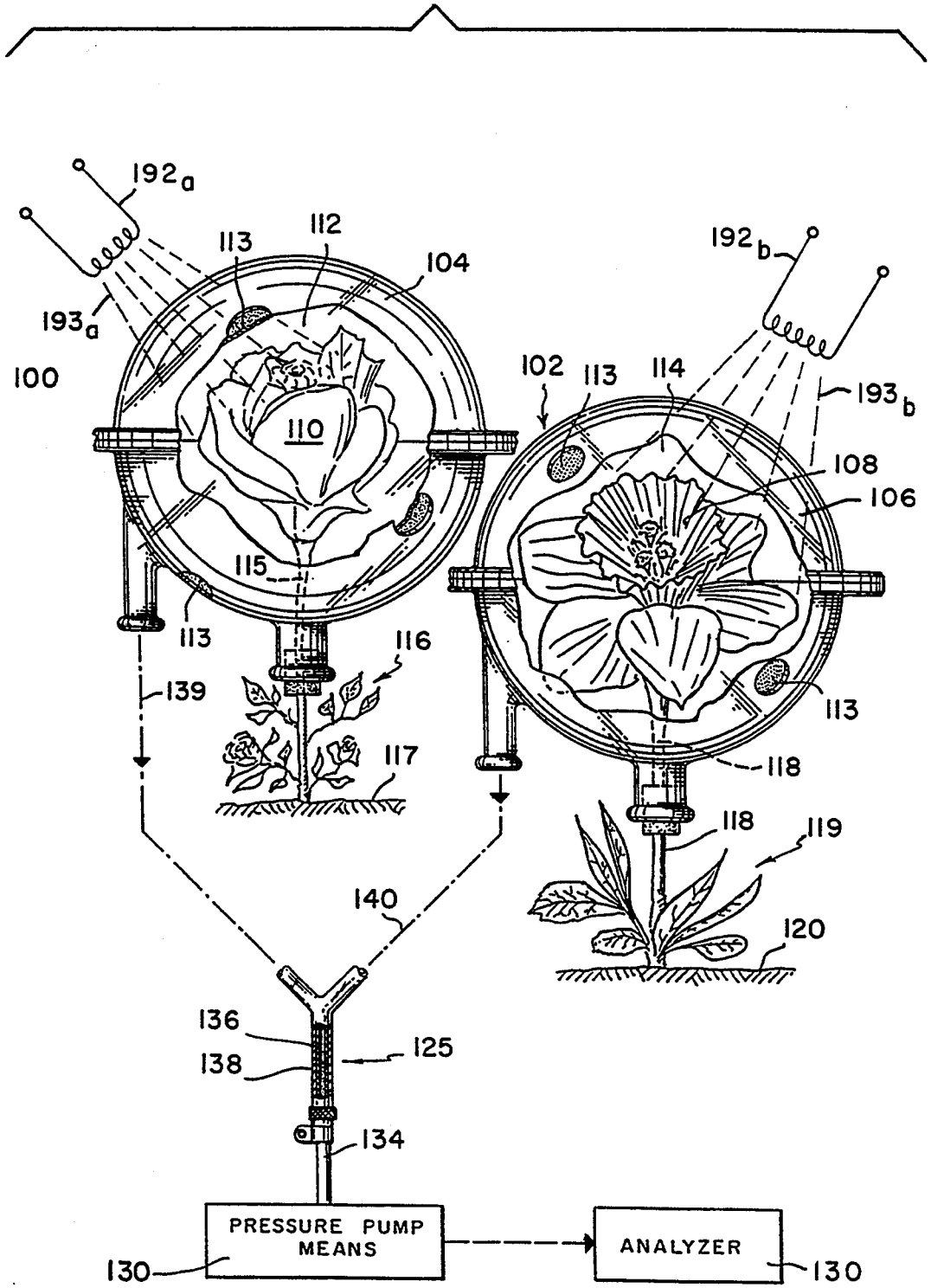
FIG.1-B

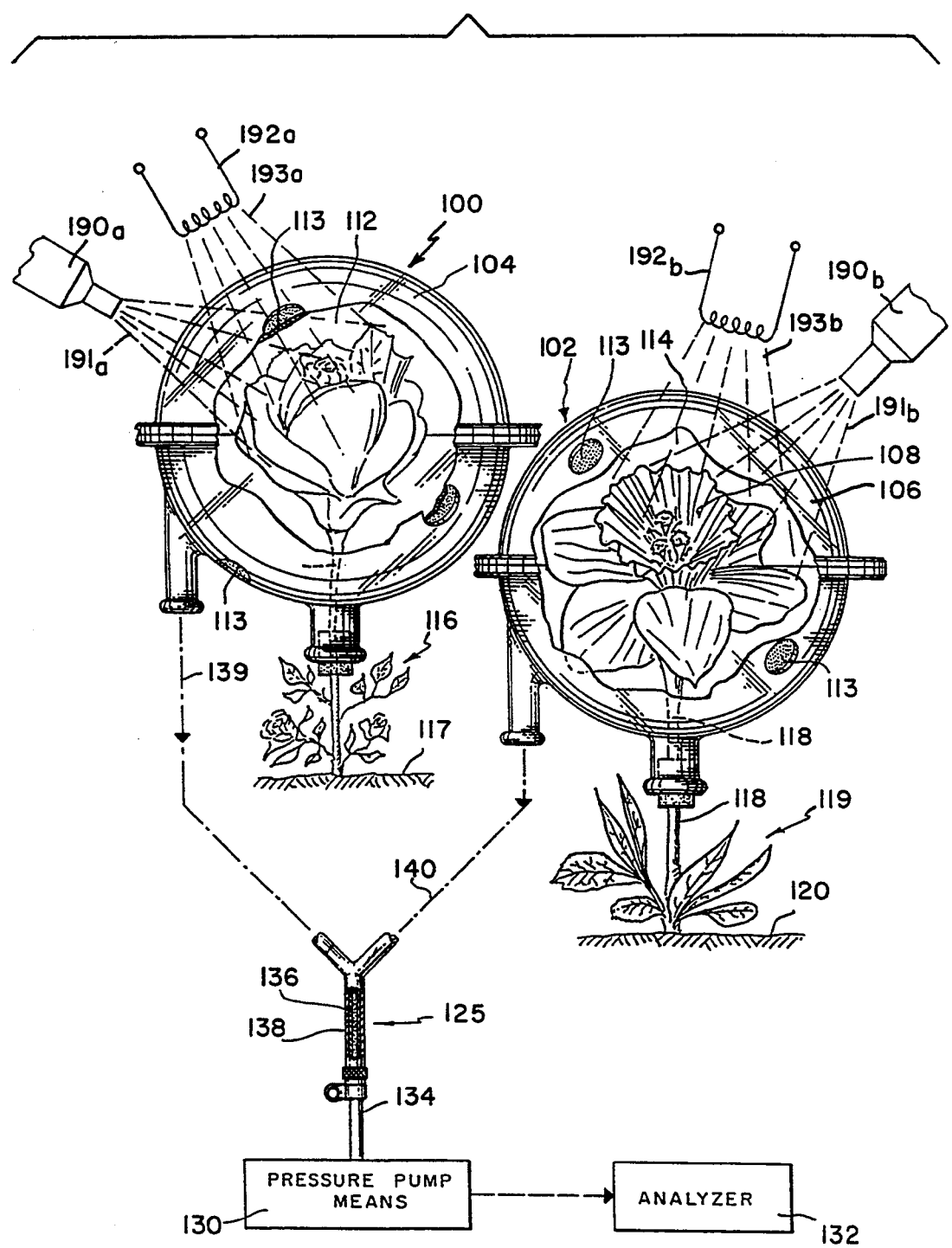

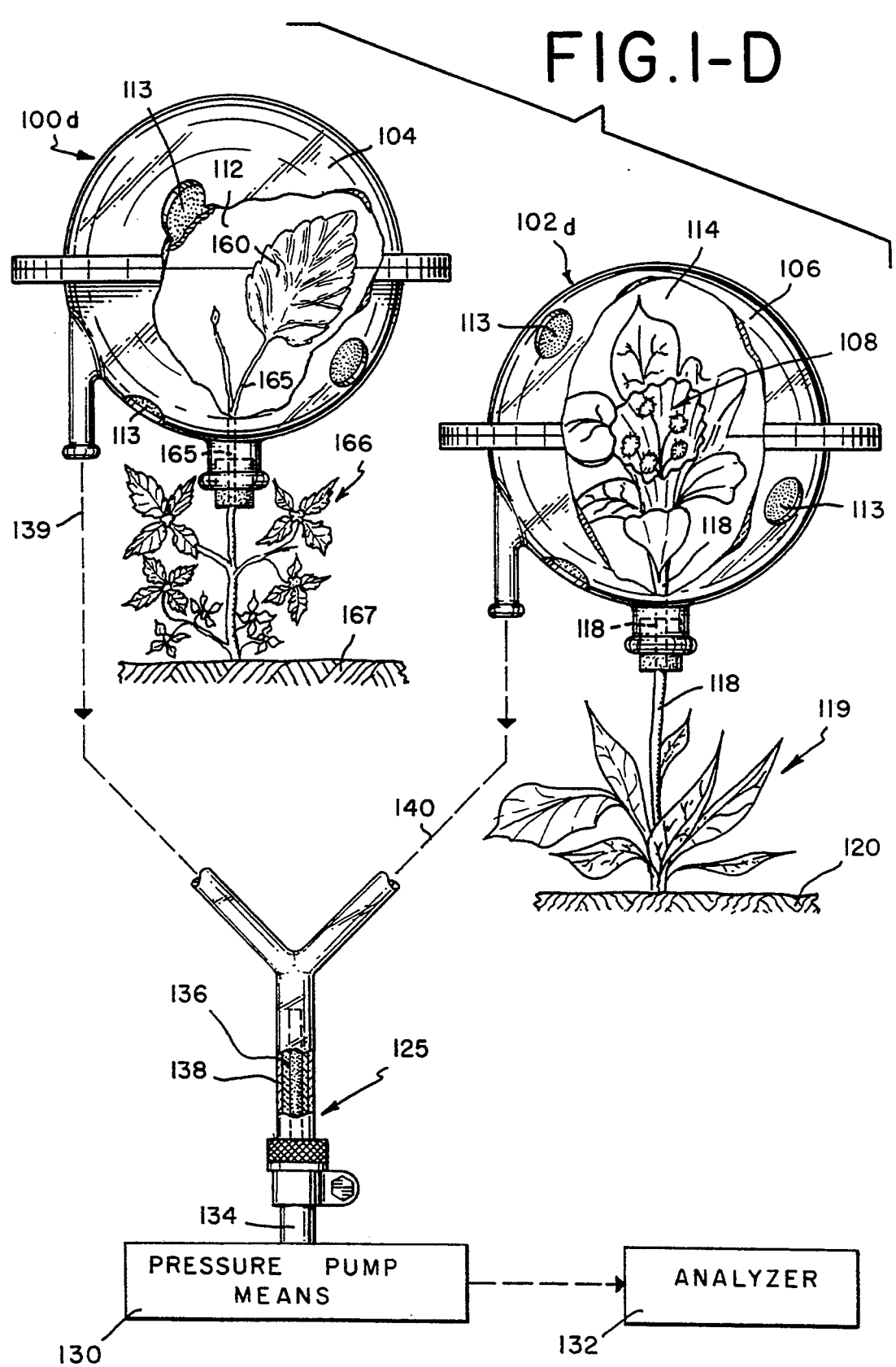
FIG. I-D

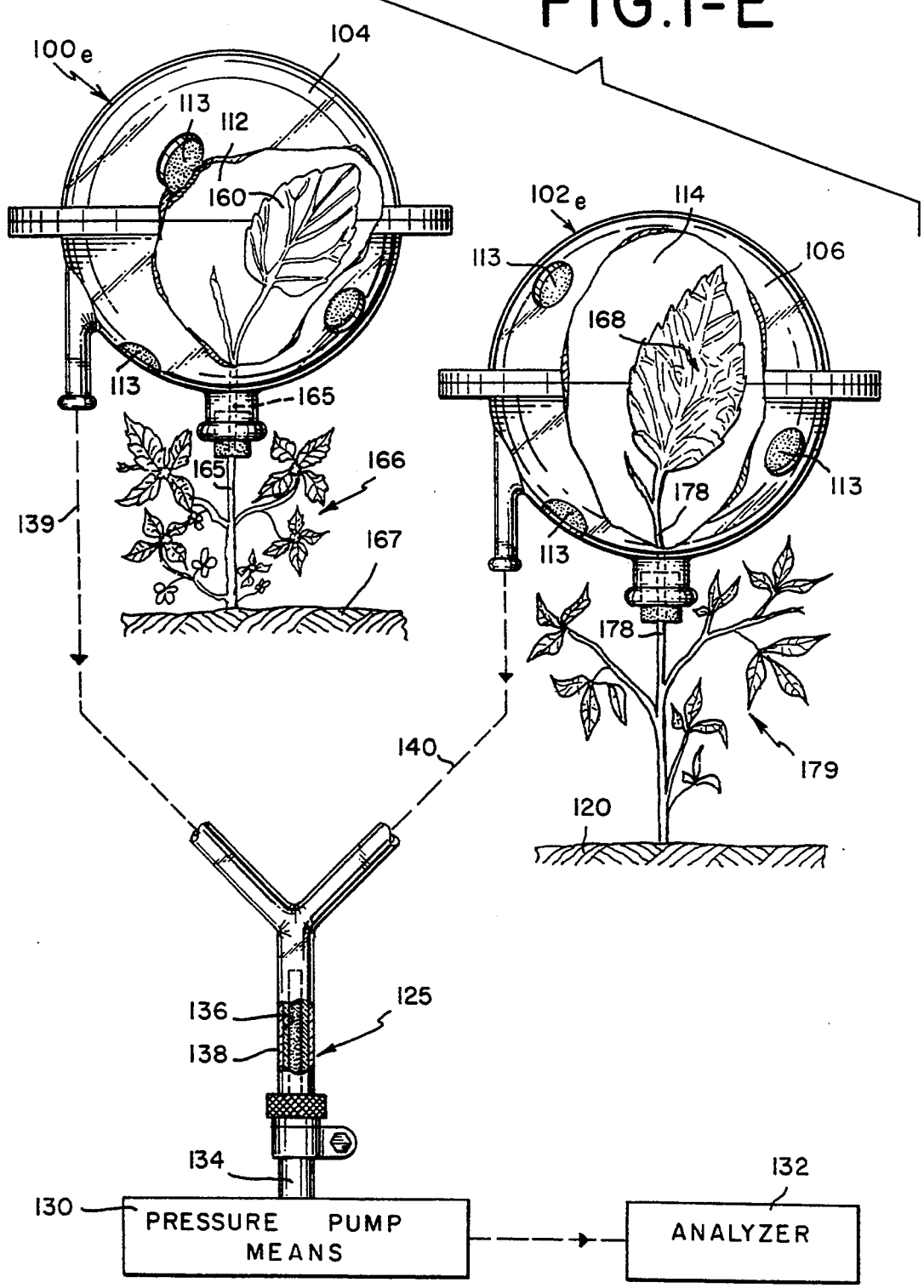
FIG.1-E

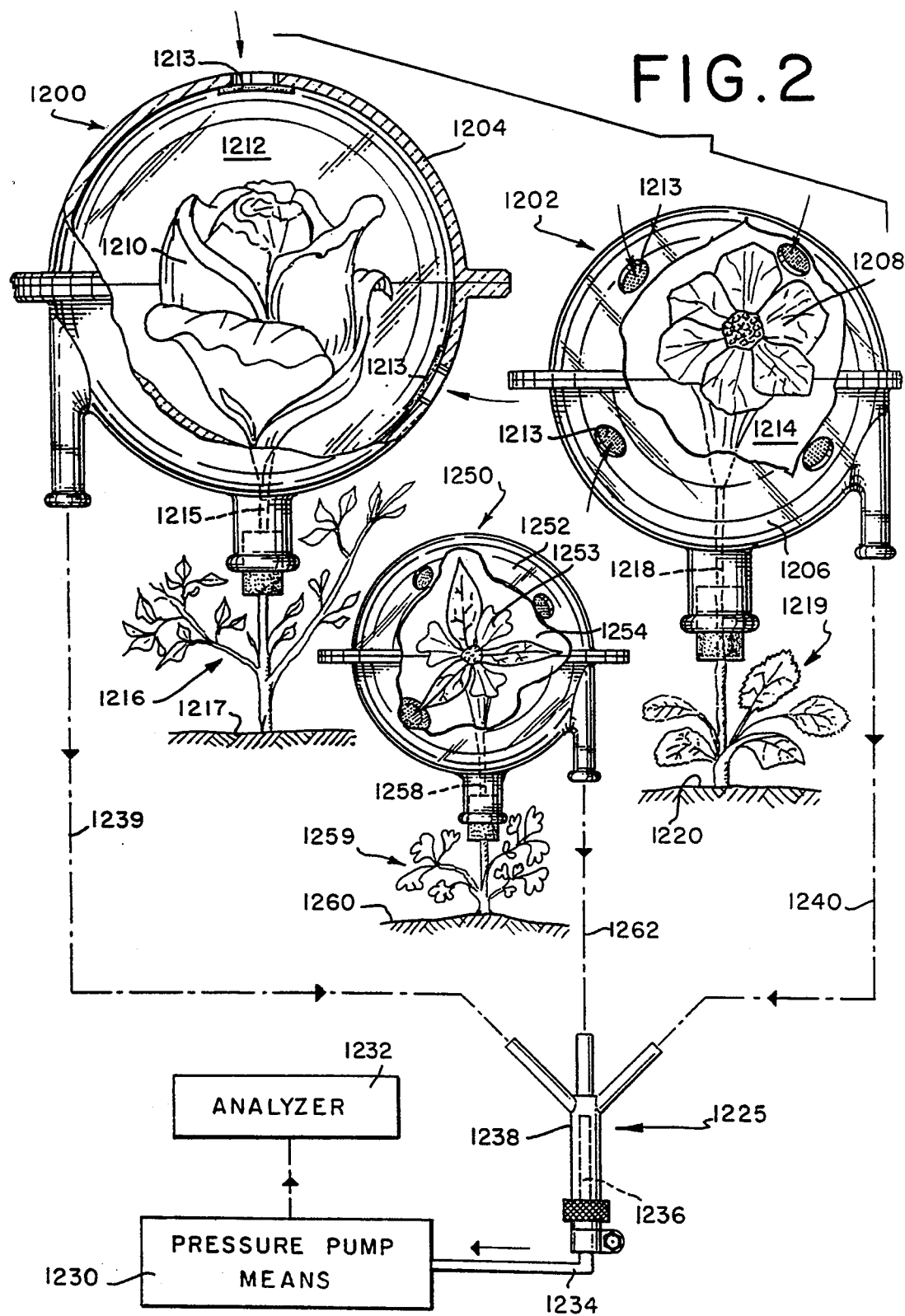

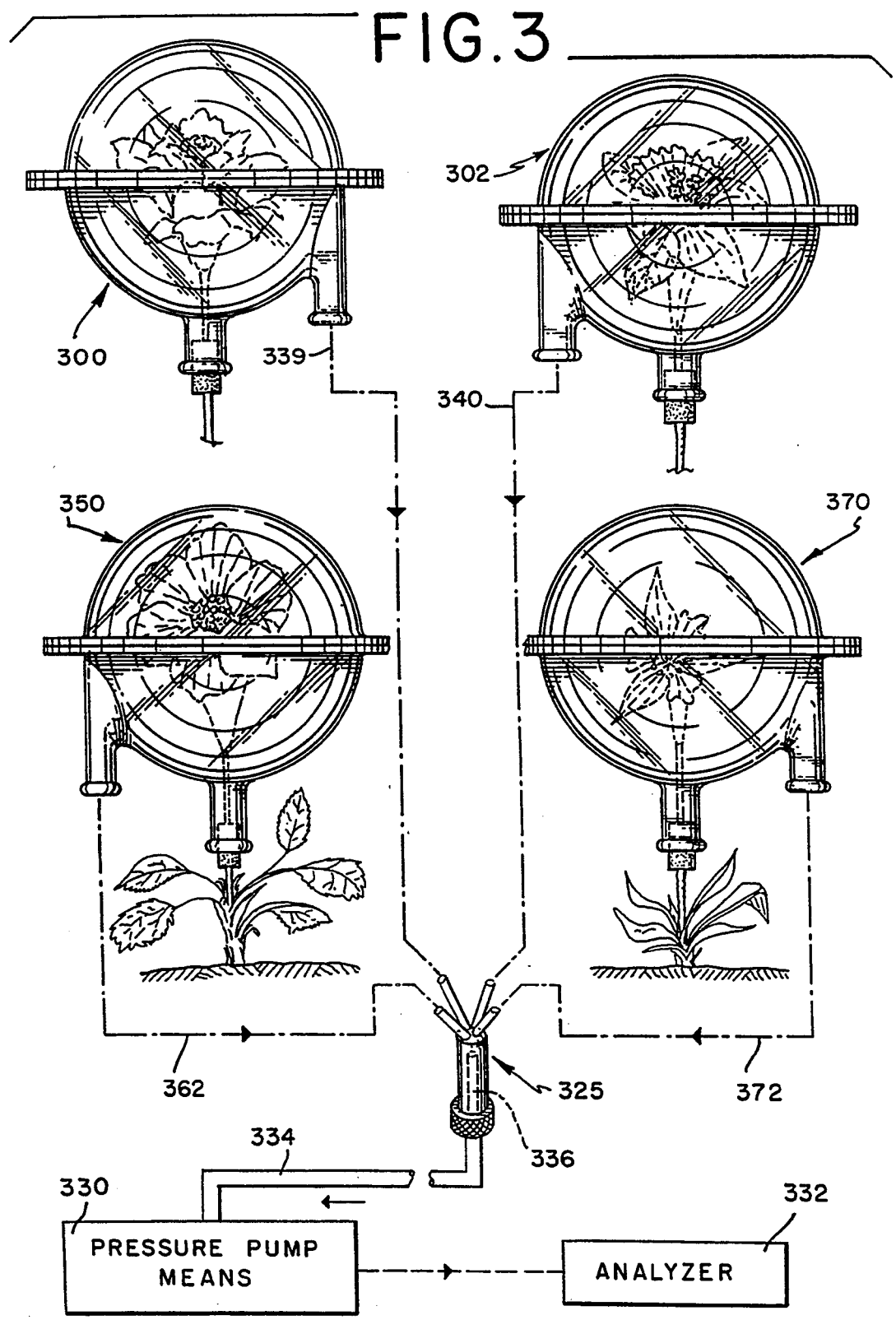

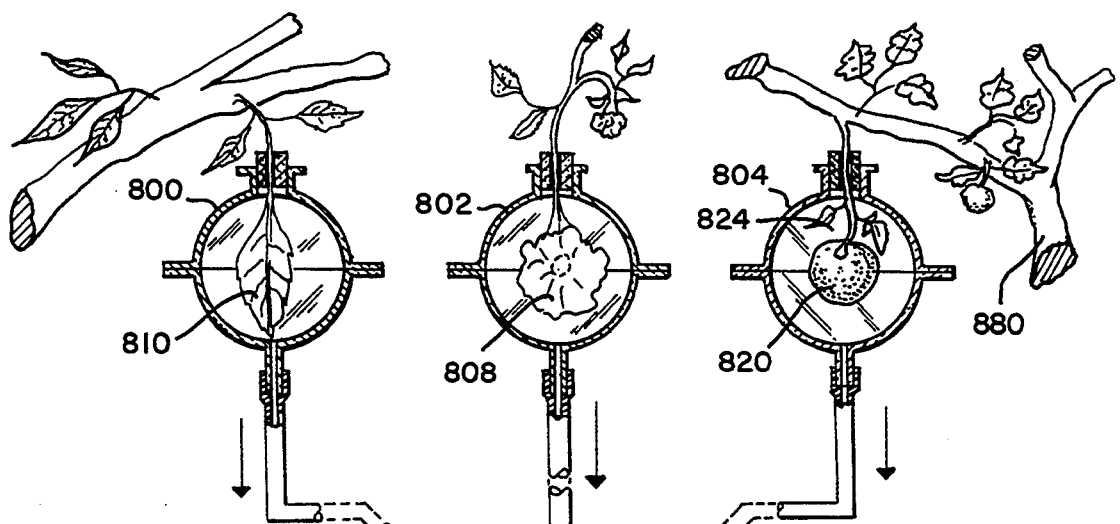
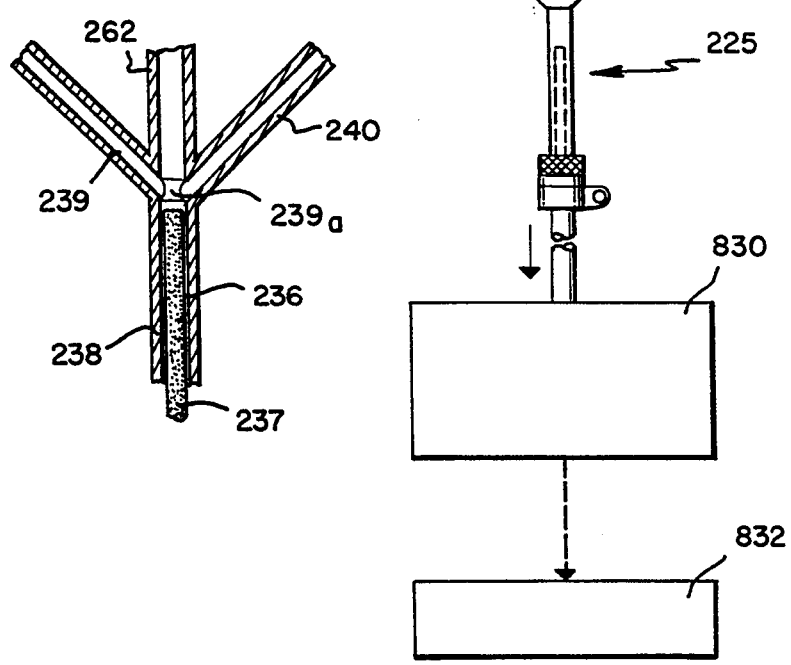
FIG.8-A
FIG.8

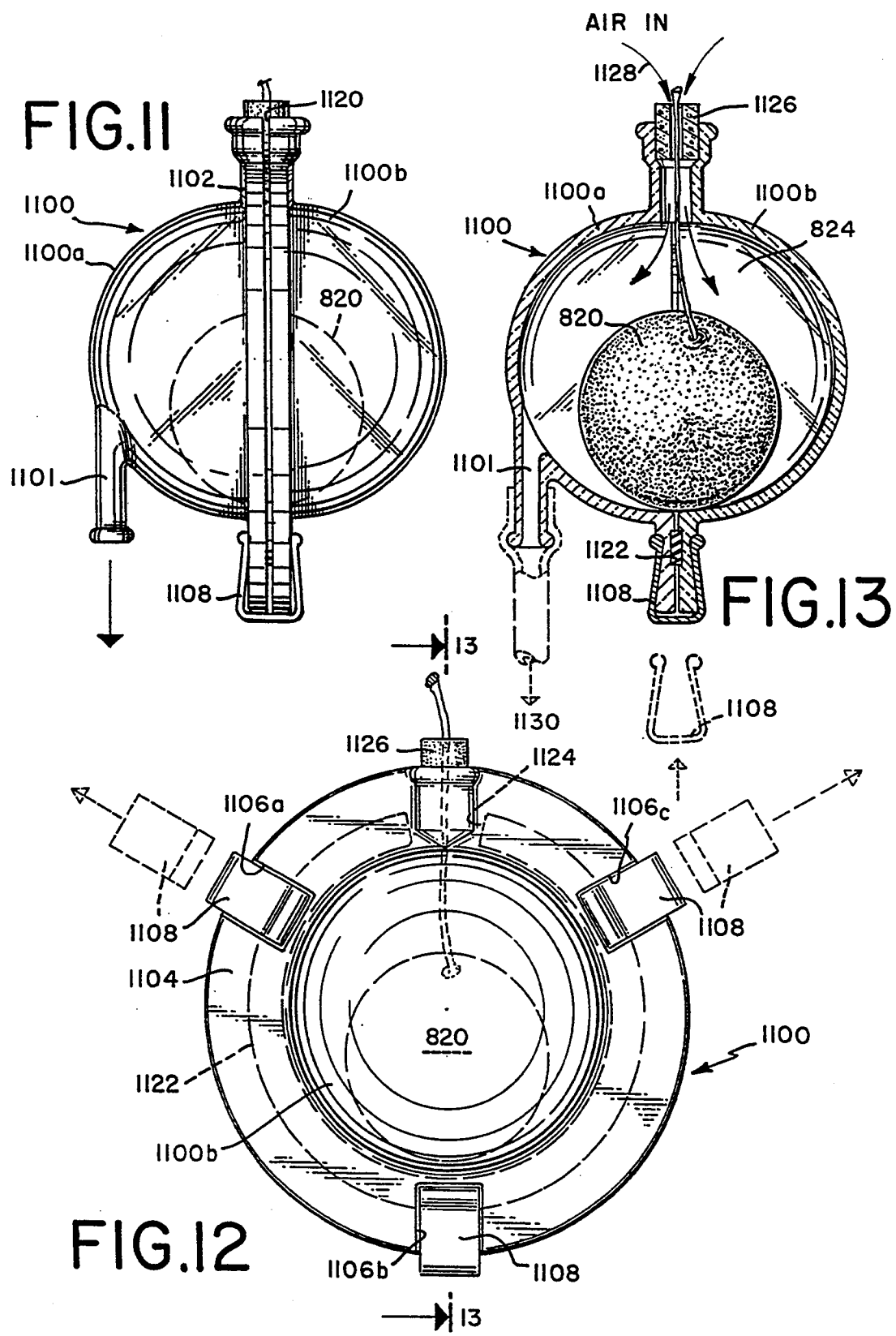

FIG.14
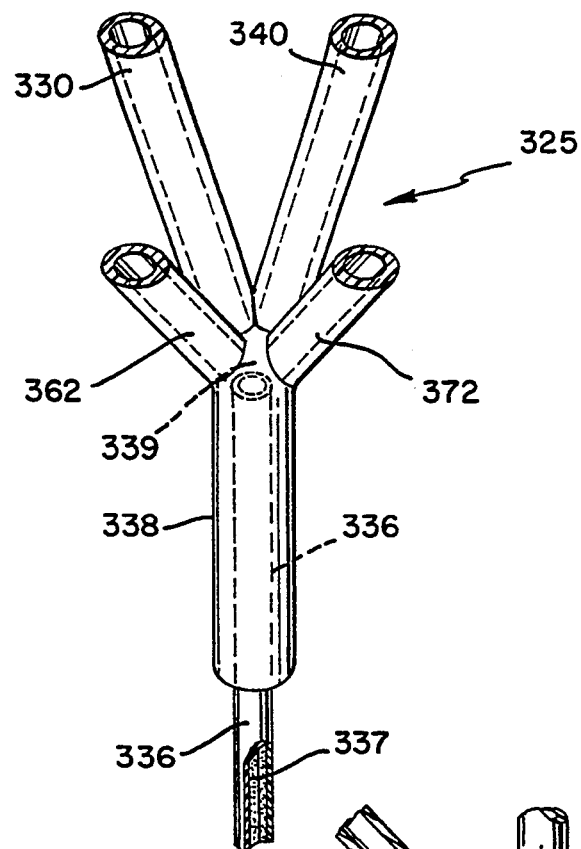
FIG.15
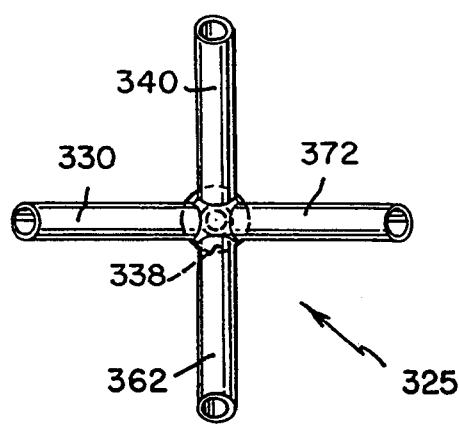
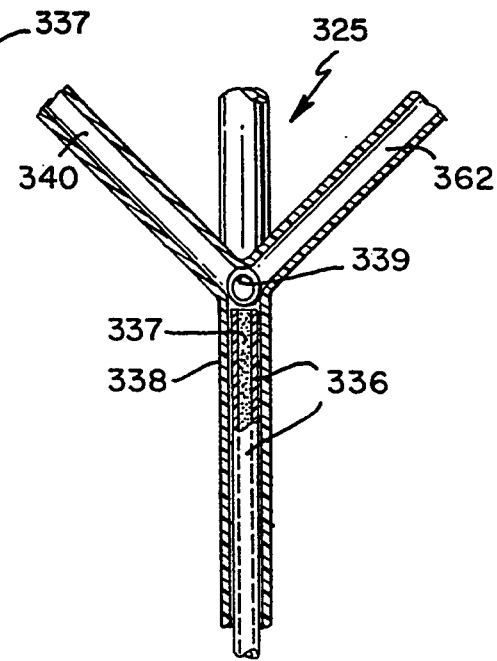
FIG.16

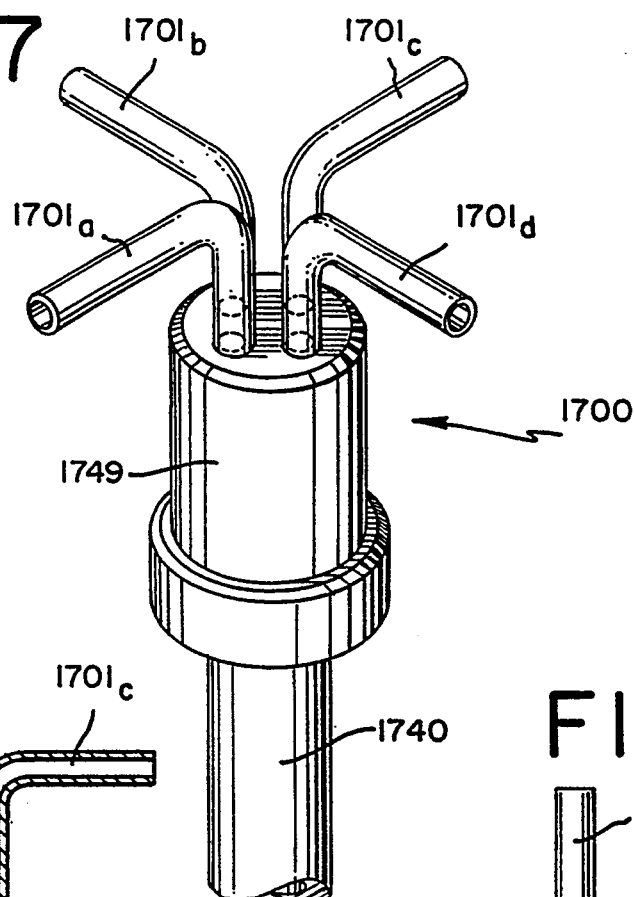
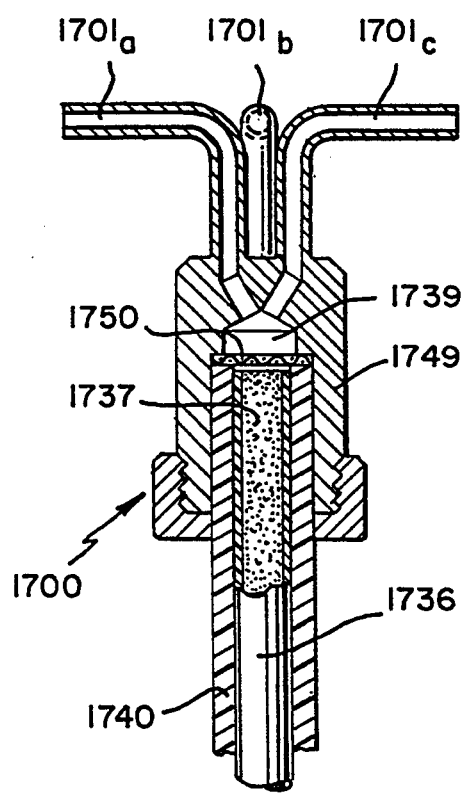
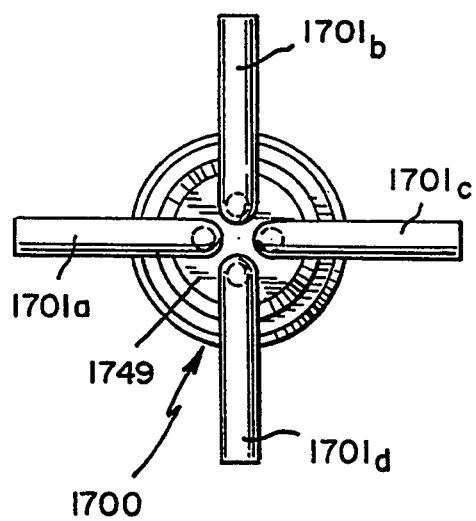
FIG.17
FIG.19
FIG.18

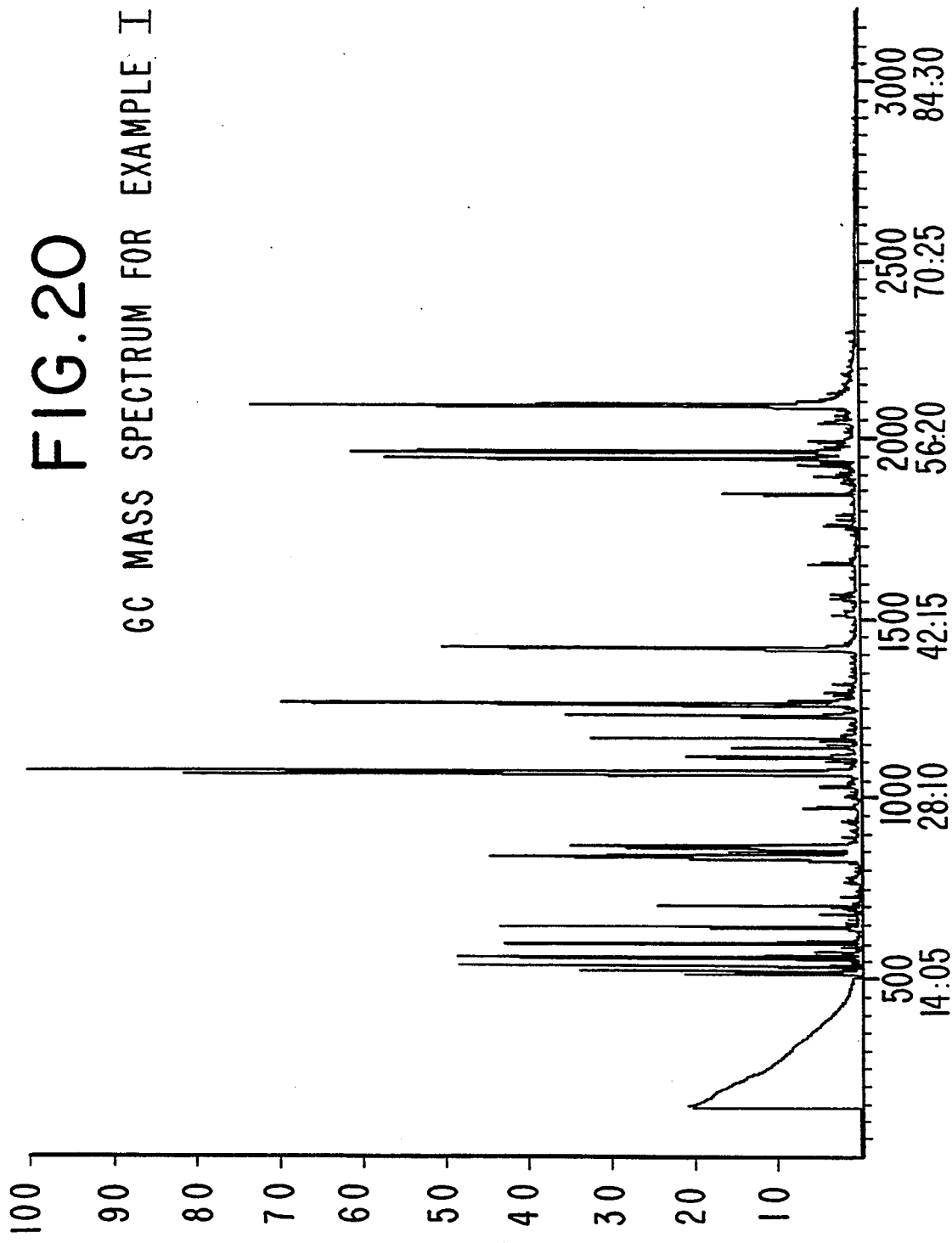

GC MASS SPECTRUM FOR EXAMPLE II.

GC MASS SPECTRUM FOR EXAMPLE III.

GC MASS SPECTRUM FOR EXAMPLE IV

AROMA EMISSION ANALYSIS SYSTEM USING A MULTIPLICITY OF INDIVIDUAL ENCLOSURES

This is a continuation in part (CIP) of U.S. patent application Ser. No. 08/092,463 filed Jul. 16, 1993, which application for patent is still pending at this time, which is a CIP of U.S. patent application Ser. No. 07/988,377, filed Dec. 9, 1992, and now issued as U.S. Pat. No. 5,269,169, filed Dec. 14, 1993.

BACKGROUND OF THE INVENTION

Our invention concerns a process for qualitatively and quantitatively substantially continuously analyzing the aroma emitted and rates of emission of the aroma components thereof from two or more different varieties and/or species of living flowers, living fruits, living trees or living leaves at a given point in time over a given time period using a multiplicity of enclosures each containing one or more living flowers, living fruits or living leaves or covering surface portions of living trees or living fruits, having a single aroma trapping means communicating with all of the enclosures; and apparatus for carrying out such a process. Our invention also concerns a process for preparing one or more perfume compositions comprising the steps of carrying out the aforementioned analysis or analyses and then, using the results of such analysis or analyses providing and admixing at least the major components found in the analysis, apparatus for carrying out such process, perfume compositions prepared using such apparatus and process, and perfumed articles and colognes containing such perfume compositions.

Uses of aromas evolved from living flowers which are parts of living plants or which are parts of living trees (e.g., cherry blossoms) or living fruits, or living leaves which are parts of living trees are highly sought after in the perfumery and flavor arts. Great difficulty has been experienced in attempting to capture and reproduce actual aroma ingredients of such living flowers at various points in time relative to the maturation of the plant or tree on which the living flower or living leaf or living fruit is growing.

In addition, a need has arisen for observation of the growth of living flowers, leaves, fruits and trees and a need for measuring such growth, standardizing the measurements of such growth at various times of plant, fruit or tree maturation and observing such growth; in an effort to optimize the creation and subsequent marketing of perfume and flavor compositions based on living flower, leaf, fruit or tree components.

Mookherjee, et al, J.Ess.Oil Res., Volume 2, pages 85–90, (March/April 1989) title "Live vs. Dead. Part II, A Comparative Analysis of the Headspace Volatiles of Some Important Fragrance and Flavor Raw Materials" sets forth an examination of the headspace volatiles of living and picked tea rose, narcissus, osmanthus and spearmint comparatively using TENAX® as the trapping adsorbent and GC/MS analysis ("Gas Chromatography/Mass Spectral Analysis") as the method of analysis. Mookherjee, et al discloses that it was found that the living rose possessed cis-3-hexenyl acetate (20.67%) as the major volatile component, whereas the major volatile component of the picked rose was 3,5-dimethoxy toluene. Mookherjee, et al further states that living narcissus flowers were found to contain benzyl acetate (44.0%), 3,4- and 3,5-dimethoxy toluene (35.0%) and indole (5.0%) whereas picked flowers contain benzyl acetate (30.43%), 3,4- and 3,5-dimethoxy toluene (18–39.5%) and indole (0.3–1.0%). Mookherjee, et al further states that osmanthus flowers (living) were found to possess beta-damascenone, dihydro-beta-ionol, and 4-keto-beta-ionone whereas these compounds were not detected in either air or nitrogen-purged picked flowers. Mookherjee further states that harvested spearmint possessed carvone (70.0%) and limonene (2.0%) in its headspace while the headspace of living spearmint was found to contain carvone (24.0%) and limonene (18.0%). Thus, Mookherjee, et al demonstrated that dramatic chemical changes take place in a plant or flower once it is harvested.

What is not disclosed in the prior art is the fact that when two or more different varieties and/or species of living flowers, leaves, fruits, surface portions of trees or surface portions of fruits are simultaneously placed in individual enclosed 3-spaces, and analyzed using a single trapping device, the resulting aroma is different in kind from that of each of the separate living flowers, leaves, fruits, surface portions of trees or surface portions of fruits and such difference gives rise to unexpected, unobvious and advantageous perfume and flavor compositions which have unobvious natural aroma and taste qualities (that is, topnotes, middle noes and undertones).

U.S. Pat. No. 5,136,805 issued on Aug. 11, 1992 describes an air-tight flexible transparent container containing at least one living flower immersed in an aqueous suspension. Described in U.S. Pat. No. 5,136,805 is an article useful (i) for display purposes; and/or (ii) for analysis of the headspace in the container above the living flower when the container is fitted with a tube effecting communication of-the internal 3-space (internal volume) of the container with outside analytical means and/or (iii) for aromatizing the environment surrounding the container when the container is fitted with a wick effecting communication of the internal 3-space (internal volume) of the container with the environment surrounding the container. However, U.S. Pat. No. 5,136,805 does not teach or infer a technique for quantitatively and qualitatively substantially continuously analyzing the aroma emitted and rates of emission of the components thereof of two or more varieties and/or species of living flowers, living fruits, living leaves or living trees growing from living plants or living trees in a natural habitat where the plants or trees bearing such flowers, leaves or fruits are outside of the enclosure containing the living flowers, living fruits, living leaves or surface portions of living trees or living fruits.

THE INVENTION

Our invention covers a process for simultaneously quantitatively and qualitatively substantially continuously analyzing the aroma emitted and rates of emission of the aroma components thereof from two or more different varieties and/or species of living flowers, living leaves, living fruits or surface portions of living fruits connected via stems to living trees and/or living plants, or surface portions of the bark of living trees, at a given point in time over a given period of time using a multiplicity of enclosures, each of which contains solely one or more of the living flowers, living fruits, or living leaves or a surface portion of a living fruit or a surface portion of a living tree. The living flowers, living fruits or living leaves are attached within the enclosures to small portions of their stems. All of the enclosures communicate with one single trapping means communicating via separate channels with each enclosure. Our invention also covers apparatus and its sub-combinations for carrying out such process. Our invention is also intending to cover a process for preparing one or more perfume compositions or flavor compositions comprising the steps of carrying out the aforementioned analysis or analyses and then using the results of such analysis or analyses: (1) providing; and (2) admixing at least one of the major components found in the analysis or analyses. Our invention is further intended to cover apparatus for carrying out such process as well as perfume compositions and flavor compositions prepared using such apparatus an process and perfumed articles and colognes containing such perfume compositions and flavor compositions.

Thus, for example, our process for simultaneously quantitatively and qualitatively analyzing the emitted aroma and rates of emission of the aroma components thereof from two or more different species and/or varieties of living flowers concerns such groups of species and/or varieties of living flowers as follows:

Group A
*Rosa Centifolia*
*Rosa gallica officinalis*
Flowers of the Rose Plant "Ausleap" as disclosed in U.S. Plant Pat. 8153 issued on February 23, 1993, the specification for which is incorporated by reference herein.
Flowers from the Rose Plant- "Auscrim" as disclosed in U.S. Plant Pat. 8154 issued on February 23, 1993, the specification of which is incorporated herein by reference.
Flowers from the Gazania plant called "Moorpark Yellow" as disclosed in U.S. Plant Pat. 8161 issued on February 23, 1993 the specification for which is incorporated herein by reference.
Group B
*Crinum x powellii*
Flowers from the Carnation Plant named CFPC Day Dream as disclosed in U.S Plant Patent 8232 issued on May 18, 1993 the disclosure of which is incorporated herein by reference.
Flowers from the Chrysanthemum Plant- Alhacultivar disclosed in U.S. Plant Pat. 8227 issued on May 11, 1993 the specification for which is incorporated by reference herein.
Group C
*Mahonia japonica*
Flowers from the Rose Plant- "Ausram" as disclosed in U.S. Plant Pat. 8156 issued on February 23, 1993 the disclosure for which is incorporated herein by reference.
Flowers from the Rose Plant- "Ausmit" as disclosed in U.S. Plant Pat. 8157 issued on February 23, 1993 the specification for which is incorporated herein by reference.
Flowers from the Rose Plant- "Poulbero Variety" as disclosed in U.S. Plant Pat. 8230 issued on May 18, 1993 the disclosure for which is incorporated herein by reference.
Group D
*Viola odorata* (sweet violet)
Flowers from the Rose Plant- "Jacsos" as disclosed in U.S. Plant Pat. 8235 issued on May 25, 1993 the disclosure for which is incorporated by reference herein.
Flowers from the Chrysanthemum Plant- "Funrise Cultivar" as disclosed in U.S. Plant Pat. 8241 issued on May 25, 1993 the disclosure for which is incorporated herein by reference.
Flowers from the Miniature Rose Plant- "Meinochot Variety" as disclosed in U.S. Plant Plant 8242 granted on June 1, 1993 the disclosure for which is incorporated herein by reference.
Flowers from the Chrysanthemum Plant named "Dark Eyes" as disclosed in U.S. Plant Pat. 8244 issued on June 1, 1993 the disclosure for which is incorporated herein by reference.
Group E
White Jasminum Nitidum
Peach Colored Rose Fragrant Delight
Group F
Yellow Osmanthus Olive
Peach Rose Fragrant Delight
Group G
Ginger Lily Flower
Jasminum Odoratissimum Flower
Group H
Purple Heliotroprium Iowa
Jasminum Odoratissimum Flower
Group J
Dwarf Navel Orange Flower
Jasmin Nitidum Flower
Group K
Red Rose All That Jazz
White Ginger Lily Flower.

Furthermore, each of the living flowers, living fruits or living leaves is attached through a stem to a living plant or a living tree. A plurality of "n" members of the living flower, living fruit and/or living leaf group is located within a plurality of fn totally enclosed 3-spaces, each having an outer side and an inner side, the inner side entirely surrounding one or more of the "n" living flowers, living leaves, and/or living fruits. The term "f" represents the ratio of the number of enclosures to the total number of living leaves, living fruits and/or living flowers being analyzed. Examples of a "totally enclosed 3-space" are:
  a sphere;
  a bifurcated sphere;
  a right circular cylinder;
  a right circular cone;
  an ellipsoid;
  a frustum of a right circular cone; or a tetrahedron. The process of our invention covers the steps of:

(a) providing at least two hollow enclosures each of which has (i) an outer wall containing an least two outer wall orifices including a first wall orifice and a second wall orifice; (ii) an inner 3-dimension space providing for the separate individual unobstructed maintenance of at least one single living fruit and/or living leaf and/or living flower; or a portion of the outer surface of a living fruit or a portion of the outer surface of the bark of a living tree;

(b) causing the insertion of at least one living fruit variety or species or a living leaf variety or species or a living flower variety or species separately, through each orifice of each hollow enclosure or causing one or more of said hollow enclosures to be sealably affixed at one of its orifices to a portion of the surface of the bark of a living tree or tip a portion of the surface of a living fruit;

(c) causing an orifice of each of said hollow enclosures to be engaged with and juxtaposed to a substantially cylindrical feeding tube having an outer feeding tube end having a substantially circular rim tightly fitted at its rim into said orifice of said enclosure arid a lower feeding tube end having a substantially circular rim jointly and sealably affixed at its rim and communicating with a common hollow totally enclosed volumetric mixing junction to the upper rim of the upper opening of a substantially cylindrical key tube, said key tube being a hollow substantially cylindrical tube having an internal key tube diameter and a key tube length and having an upper key tube opening having an upper substantially circular key tube rim and a lower key tube opening having a lower substantially circular key tube rim with a trapping cylinder contained (i) partially within said key tube and (ii) extending beyond said lower key tube opening, said trapping cylinder being substantially concentric with said key tube, said trapping cylinder consisting of a hollow cylindrical tube containing a trapping material for trapping volatiles, having an outer trapping tube diameter substantially less than the inner key tube diameter, the space between the key tube and trapping cylinder being sealed in a gas-tight fashion;

(d) causing a vacuum pumping means to be juxtaposed with, and engaging said lower end of said trapping tube means whereby said vacuum pumping means exerts a negative pressure on each of said enclosed 3-dimensional spaces whereby all of said aroma components are transmitted from each of said 3 dimensional spaces of said hollow enclosures into said trapping tube;

(e) removing the trapping material from he trapping tube;

(f) extracting the aroma components from the trapping material; and (g) carrying out a qualitative and quantitative analysis of said aroma components.

The foregoing steps (d), (e), (f) and (g) may, if desired, be carried out over a period of time, repetitively, at the end of specific time intervals, for example, every hour or every day for a period of one, two or three weeks.

Also covered in our invention is a process for preparing a perfume composition or a flavor composition which comprises the steps of carrying out the above process followed by providing from at least one independent source at least the major aroma or flavor components found by the analysis of step (g) and then admixing the resulting components to form a perfume or flavor composition.

The process of our invention may be further modified wherein radiation from one or more radiation sources such as an infrared radiation source and/or an ultraviolet radiation source connected to an electric power supply is emitted in a direction from one or more radiation sources and is directed into one or more of the totally enclosed 3-spaces each containing one or more living flowers and/or living leaves and/or living fruits or each enclosing a partial surface of a living fruit or the bark of a living tree. The radiation source(s) can be a plurality of sources directed to individual enclosed 3-spaces containing individual or a plurality of living flowers and/or living fruits and/or living leaves or enclosing a partial surface of a living fruit or the bark of a living tree or a single radiation source or multitude of radiation sources greater than the number of enclosed 3-spaces containing individual or a plurality of living flowers and/or living fruits and/or living leaves or enclosing a partial surface of a living fruit or the bark of a living tree. The use of such infrared or ultraviolet radiation will give rise to an alteration in the aroma composition and hence the aroma components trapped, evolved by the living flower(s) and/or living leaves and/or living fruits contained within each of the enclosed 3-spaces or by the partially enclosed sections of the living fruit surfaces or living tree bark surfaces.

Furthermore, a plurality of separate perfume and flavor compositions containing at least the major components of he aromas emitted by a multitude of groups of living flowers living leaves, living trees and/or living fruits may be produced by carrying out a process comprising the steps of:

(i) carrying out the aforementioned process;

(ii) separately providing from independent sources at least the major aroma components found by analyses of each of the steps (g) of the above process; and (iii) separately admixing each of the groups of components to form separate perfume and flavor compositions.

Each enclosure of the apparatus of our invention used in the process of our invention has an inner void having a volume $V_0$ sufficient to provide for the separate individual unobstructed maintenance of each of the living flowers; and/or living fruits and/or living leaves contained therein; and the inner volume $V_0$ of each enclosed 3-space is such that the volume relationship between the volume of the inner void expressed as the $V_0$ and the volume of the 3-space surrounding each living flower, living fruit and/or living leaf in the enclosure, $V_j$ is:

$$V_o > \sum_{j=1}^{n} V_j$$

wherein $$V_j = \frac{4}{3} \pi R_j^3;$$

$$V_o > \sum_{j=1}^{n} \frac{4}{3} \pi R_j^3;$$

and $$V_o = H + \sum_{j=1}^{n} \frac{4}{3} \pi R_j^3,$$

$V_i$ having an individual mathematically constructed outer surface and $$\sum_{i=1}^{n} V_j$$

having an outer surface wherein $R_i$ represents the length of the longest petal or longest leaf of the $i^{th}$ living flower or living leaf and H is the headspace between the mathematically constructed outer surface of $$\sum_{i=1}^{n} V_j$$

and said inner wall of said enclosed 3-space.

When an enclosed 3-space is in the shape of an ellipsoid, the volume relationship:

$$V_o > \sum_{j=1}^{n} V_j$$

is such that $$V_o = 8 \int_0^{\sqrt{\frac{k}{a}}} \int_0^{\sqrt{\frac{k^2}{b} - \frac{ax^2}{b}}} \int_0^{\sqrt{\frac{k^2}{c} - \frac{ax^2}{c} - \frac{by^2}{c}}} dzdydx$$

wherein the equation for the ellipsoid is:

$$ax^2 + by^2 + cz^2 = k^2$$

wherein a, b, c and k are the same or different numerical constants and wherein x is a dimensional variable measuring horizontal distance from the geometric center of the ellipsoid to the inner side of the hollow enclosure; wherein y is a dimensional variable measuring vertical distance from the geometric center of the ellipsoid to the inner side of the hollow enclosure; and wherein z is a dimensional variable measuring depth distance from the geometric center of the ellipsoid to the inner side of the hollow enclosure.

The relationship from a mathematical standpoint of the diameter, $D_0$ and volume $V_0$ of a totally enclosed 3-space to the diameter $D_i$ and volume $V_i$ of the individual mathematically constructed outer surface of the $i^{th}$ living flower, $i^{th}$ living fruit, and/or $i^{th}$ living leaf is shown in the following equations:

$$D_{oMIN}^3 = 1.5 \sum_{j=1}^{n} D_j^3$$

$$D_{oMAX} = 15 \sum_{j=1}^{n} D_j^3$$

$$V_{oMIN} = 1.5 \sum_{j=1}^{n} V_j$$

$$V_{oMAX} = 15 \sum_{j=1}^{n} V_j$$

and $$1.5 \sum_{j=1}^{n} V_j \leq V_o \leq 15 \sum_{j=1}^{n} V_j$$

A preferable empirical function is:

$$D_o = [1.09 + 0.01\, n_j] \sum_{j=1}^{n_i} D_j$$

wherein $n_i$ represents the number of living flowers, living leaves and/or living fruits within a given enclosed 3-space. The symbol:

$$\sum_{j=1}^{n} D_j$$

represents the arithmetic sum of the mathematically constructed diameters of each living flower and/or living leaf and/or living fruit enclosed within a single totally enclosed 3-space.

When the one or more totally enclosed 3-space walls is fabricated of a semi-rigid transparent substance such as a polyacrylate or polymethacrylate such as polyethylmethacrylate or polymethylmethacrylate or copolymers of methylmethacrylate, ethylmethacrylate and ethylene, then the volume $V_0$ will be subject to change according to the equation:

$$V_0 = V_{01} \Delta V_0$$

wherein the symbol $V_{01}$ is the initial volume and the symbol $\Delta V_0$ is the change in volume. This change in volume is shown by the equation $$\Delta V_o = \int_{\theta_1}^{\theta_2} \frac{\left[\left(\frac{\partial v}{\partial \theta}\right) + \left(\frac{\partial \Sigma V}{\partial \theta}\right) + \left(\frac{\partial T}{\partial \theta}\right) + \left(\frac{\partial P}{\partial \theta}\right)\right] d\theta}{+ \int_{\theta_1}^{\theta_2} \left[\frac{\partial^2 m}{\partial \theta^2}\right] d\theta}$$

where it is assumed that the original volume $V_0$ is: $V_0$ is:

$$V_o = f\left(v, \sum_{j=1}^{n} V_j, T, P, \frac{\partial m}{\partial \theta}\right)$$

wherein the symbol $$\sum_{i=1}^{n} V_j$$

is such that $$V_j = \frac{4}{3} \pi R_j^3$$

wherein $R_i$ is the length of the longest petal of the living $i^{th}$ flower or the length of a living leaf in the enclosure; and if one or more living leaves and/or living flowers are in the same enclosure then $R_i$ is the length of the longest petal or longest leaf int he enclosure, and the term:

$$\sum_{i=1}^{n} V_j$$

represents the total mathematically constructed spherical volumes surrounding the group of living flowers and/or living leaves and/or living fruits in the enclosed 3-space; P represents pressure; T represents temperature; v represents the air velocity within the totally enclosed 3-space and the symbol:

$$\frac{\partial m}{\partial \theta}$$

represents the partial derivative of the mass transfer of aroma components per unit time from the living flower and/or living leaf and/or living fruit to the trappng substance. The symbol: $\theta$ represents time. The symbol: $\theta_1$ represents initial time and the symbol: $\theta_2$ represents the time at the end of the measurement. The symbol:

$$\frac{\partial v}{\partial \theta}$$

is actually:

$$\left( \frac{\partial v}{\partial \theta} \right)_{P,T,\frac{\partial m}{\partial \theta}, \Sigma V}$$

and is the partial derivative of air velocity with respect to time. The symbol:

$$\frac{\partial \Sigma V}{\partial \theta}$$

is actually:

$$\left( \frac{\partial \sum_{j=1}^{n} V_j}{\partial \theta} \right)_{P,T,v,\frac{\partial m}{\partial \theta}}$$

and is the partial derivative of the mathematically constructed individual living flower and/or living leaf and/or living fruit volume sum with respect to time. The symbol:

$$\frac{\partial T}{\partial \theta}$$

is actually:

$$\left( \frac{\partial T}{\partial \theta} \right)_{P,v,\Sigma V_j, \frac{\partial m}{\partial \theta}}$$

and is the partial derivative of temperature with respect to time. The symbol:

$$\frac{\partial P}{\partial \theta}$$

is actually:

$$\left( \frac{\partial P}{\partial \theta} \right)_{v,T,\Sigma V_j, \frac{\partial m}{\partial \theta}}$$

and is the partial derivative of internal pressure within the enclosed 3-space with respect to time. The symbol:

$$\frac{\partial m}{\partial \theta}$$

is actually:

$$\left( \frac{\partial m}{\partial \theta} \right)_{P,T,v,\Sigma V_j}$$

The symbol:

$$\frac{\partial^2 m}{\partial \theta^2}$$

is actually:

$$\left[ \frac{\partial^2 m}{\partial \theta^2} \right]_{P,T,v,\Sigma V_j}$$

and is the partial derivative of the rate of mass transfer of aroma components from the living flower and/or living leaf and/or living fruit to the entrapment material with respect to time.

By the same token, the apparatus of our invention for qualitatively and quantitatively analyzing the emitted aroma and rates of emission of the aroma components thereof from two or more different varieties and/or species of living leaves, living flowers, living trees and/or living fruits at a given point in time or over a given period of time, using separate enclosures, one or more of which each contain one single living flower or one single living fruit or one single living leaf and/or one or more of which separately covers a portion of the outer surface of the bark of a living tree and/or one or more of which covers a portion of the outer surface of a living fruit and having a single aroma trapping means communicating in manifold fashion with all of the single enclosures comprises:

(a) two or more hollow enclosures each of which has
 (i) an outer wall containing at least two outer wall orifices spaced at a finite distance from one another including a first outer wall orifice and a second outer wall orifice;
 (ii) an inner three dimensional space providing for the separate maintenance of at least one single living fruit and/or living leaf and/or living flower or a portion of the outer surface of the bark of a living tree or a portion of the outer surface of a living fruit;
(b) having inserted into at least one of the orifices of each of said hollow enclosures at leas one living fruit variety or species and/or at least one living leaf variety or species and/or at leas one living flower variety or species and/or causing one or more of said hollow enclosures to cover at an orifice of said hollow enclosure a portion of the outer surface of a living fruit and/or at an orifice of said hollow enclosure, a portion of the outer surface of the bark of a living tree;

(c) communicating with and juxtaposed to an orifice of each of said hollow enclosures a single substantially cylindrical feeding tube each of which feeding tube has a lower rim having a substantially circular lower rim end and an outer substantially circular feeding tube end having a substantially circular outer rim sealably affixed to said orifice of said enclosure;

(d) each of said feeding tubes at said lower rim being jointly and sealably communicative and affixed at a common hollow totally enclosed volumetric mixing junction to the upper rim of the upper opening of a single key tube, the key tube being a hollow substantially cylindrical key tube having an internal key tube diameter and a key tube length and having an upper key tube opening having an upper substantially circular rim and a lower key tube opening having a lower substantially circular rim with;

(e) a trapping cylinder contained partially within said key tube and substantially concentric with said key tube, said trapping cylinder extending beyond said lower key tube opening, said trapping cylinder consisting of a hollow cylindrical tube containing trapping material for trapping volatiles emitted from said living leaf or said living fruit or said living flower or said surface portion of said living fruit or said bark surface portion of said living tree, said trapping tube having a trapping tube diameter substantially less than said key tube diameter;

(f) juxtaposed with and engaging said lower end of said trapping tube, a vacuum pumping means exerting a negative pressure on said enclosed 3-space whereby said aroma components are transmitted from said 3-space into said trapping tube means.

The aroma components-are thus absorbed or adsorbed onto said trapping material thereby forming an aroma component-bearing trapping material.

Our apparatus may also include means for removing the, aroma component-bearing trapping material from the trapping tube means; extraction means for extracting the aroma components from the aroma component-bearing trapping material thereby forming an extracted aroma component composition; and analysis means for carrying out qualitative and quantitative analysis on the extracted aroma component composition.

The apparatus may also be constructed so that one or .note radiation sources (requiring an electric power supply) is located external to and in close proximity to each of the totally enclosed 3-spaces wherein radiation from the radiation source(s) is directed into one or more of the totally enclosed 3-spaces thereby altering the rate of evolution of aroma components and the composition of the aroma being evolved by each of the one or more living flowers, living fruits, living leaves, living fruit surface sections and/or living tree bark surface sections. Furthermore, each of the totally enclosed 3-spaces or at least one of the totally enclosed 3-spaces may have baffles bonded to each of the inside walls of the totally enclosed 3-spaces causing turbulent mixing of the aroma components of the living flowers, living fruits, living leaves, living fruit surface sections and/or living tree bark surface sections as said aroma components are evolved from the living flowers, living fruits, living leaves, living fruit surface sections and/or living tree bark surface sections into the air streams prior to reaching the trapping material.

The analysis means may be GC-MS apparatus (gas chromatography/mass spectral analysis apparatus) taken alone or taken further together with infrared analysis equipment and nuclear magnetic resonance analysis equipment. In addition, Raman Spectral analysis equipment may also be used in the analysis means for analyzing the aroma components evolved by the living flowers, living fruits, living leaves, living fruit surface sections and/or living tree bark surface sections within each totally enclosed 3-space.

A subcombination apparatus of our invention consists of the analytical volatile substance trapping apparatus subcombination comprising:

(x) a hollow substantially cylindrical key tube having an internal key tube diameter and a key tube length; and having an upper key tube opening having an upper substantially circular rim and a lower key tube opening having a lower substantially circular rim;

(y) a trapping cylinder contained partially within said key tube, extending substantially beyond said lower key tube opening and substantially concentric with said key tube, said trapping cylinder consisting of a hollow cylindrical tube containing trapping material for trapping volatiles; said trapping cylinder having an outer trapping tube diameter substantially less than the inner diameter of said key tube, the space between the key tube and the trapping cylinder being sealed in a gas-tight fashion; and (z) communicating with and jointly and sealably affixed at a common hollow totally enclosed volumetric mixing junction to the upper rim of said upper opening of said key tube, a plurality of hollow substantially cylindrical feeding tubes extending in diverse directions away from said key tube upper rim, each of said feeding tubes having an outer substantially circular feeding tube rim and a lower substantially circular feeding tube rim, said lower feeding tube rim being sealably affixed to and communicating with said volumetric mixing junction, such that a continuous unbroken travel path for molecules of volatiles exists from each of said outer feeding tube rims to the said lower rim of said trapping cylinder, whereby volatiles pass through said feeding tubes in a direction towards said key tube and are entrapped in said trapping material located in said trapping tube.

Various trapping materials are useful in the practice of our invention in the trap used in trapping the aroma components emitted from within each of the totally enclosed 3-spaces by the living flowers, living fruits, living leaves, living fruit surface sections and/or living tree bark surface sections. TENAX® is a preferable material. Various forms of TENAX® are useful, for example, TENAX®-GC. TENAX® is a registered trademark of ENKA N.V. of The Kingdom of The Netherlands (CAS Registration No. 24938-68-9). Various forms of TENAX® and methods of producing same are described in the following U.S. Letters Patent, the disclosures of which are incorporated herein by reference:

U.S. Pat. No. 3,400,100 issued on Sep. 3, 1968 ("Process For The Preparation Of Polyphenylene Ethers")

U.S. Pat. No. 3,644,227 issued on Feb. 22, 1972 ("Separation Of Poly(2,6-Dimethyl-1,4-Phenyleneoxide) from its blends with other polymers")

U.S. Pat. No. 3,703,564 issued on Nov. 21, 1972 ("Bis[Polyphenyleneoxide]-Ester Block Copolymers")

U.S. Pat. No. 4,431,779 issued on Feb. 14, 1984 ("Polyetheramide-Polyphenylene Ether Blends")

U.S. Pat. No. 4,801,645 issued on Jan. 31, 1989 ("Thermoplastic Resin Composition")

TENAX®-GC is actually a polyphenyleneoxide defined according to the structure:

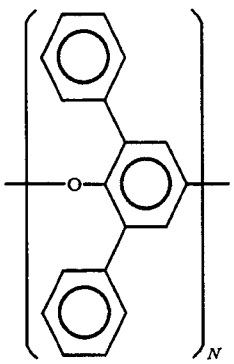

wherein N is an integer of from about 100 up to about 150.

Other trapping materials useful in the practice of out invention are as follows: Activated Carbon marketed by Aldrich Chemical Company of 1001 West Saint Paul Avenue, Milwaukee, Wisconsin 53233 (Catalog Nos. 16,155-1; 29,259-1; 24, 223-3; 24,224-1 and 24,227-6); Activated Alumina marketed by Sigma Chemical Company of St. Louis, Missouri (Catalog Nos. A8753; A8878; A9003; A1772; A1522 and A2272); Silica Gels marketed by Sigma Chemical Company, for example, Catalog Nos. S4004; S6628 and H8506; CHROMOSORB® (registered trademark of the Johns-Manville Company of Manville, New Jersey) such as CHROMOSORB® LC-1; CHROMOSORB® LC-2; CHROMOSORB® LC-3, and CHROMOSORB® LC-7 marketed by the Sigma Chemical Company under Catalog Nos. C 0641, C 0766, C 5517 and C 6269.

The negative pressure pump means of our invention useful in the practice of our invention is preferably a vacuum pump of the "Low Flow" variety, for example, a "Low Flow" pumps marketed by the Ametek Company of Largo, Florida 34643 (the Ametek Constant Flow Sampler).

At least one of the living flower, living fruit, living leaf or living tree fragrance compositions produced according to the process of our invention and one or more auxiliary perfume ingredients including, for example, alcohols, aldehydes, nitriles, esters, cyclicesters, ketones, ethers, synthetic essential oils and natural essential oils may be admixed so that the combined odors of the individual components produce a pleasant and desired fragrance particularly and preferably in the floral and/or piney fragrance area.

Such perfume compositions usually contain (a) the main note or "bouquet" or foundation stone of the composition; (b) modifiers which round off and accompany the main note; (c fixatives which include odorous substances which lend a particular note to the perfume throughout all stages of evaporation and substances which retard evaporation; and d) topnotes which are usually low-boiling, fresh smelling materials.

In perfume compositions, it is the individual components which contribute to its particular olfactory characteristics, but the overall effect of the perfume composition will be the sum of the effects of each of the ingredients, Thus, one or more of the living flower, living leaf, living fruit or living tree fragrance compositions of our invention and one or more auxiliary perfume ingredients can be used to alter the aroma characteristics of a perfume composition, for example, by utilizing or moderating the olfactory reaction contributed by at least one other ingredient in the composition.

The amount of at least one of the living flower, living leaf, living fruit or living tree fragrance compositions of our invention useful in perfume compositions for augmenting of enhancing of floral, piney, magnolia, and jasmine aromas may vary from about 1% by weight of the perfume composition up to 100% by weight of the perfume composition (the entire composition can be composed of the living flower, living Leaf, living fruit or living tree fragrance components determined by the practice of our invention)

At least one of the living flower, living leaf, living fruit or living tree compositions of our invention and, if desired, one or more auxiliary perfume ingredients can be used to impart floral aroma nuances, topnotes and undertones to soaps, anionic, cationic, nonionic or zwitterionic detergents, fabric softener compositions, fabric softener articles, cosmetic powders, hair preparations and the like. The amount employed can range up to 100% by weight of the fragrance components and can range up to approximately 0.5% of the eight of the perfumed article and will depend upon considerations of cost, nature of the end product, the effect desired on the finished product and the particular fragrance sought.

At least one of the living flower, living leaf, living fruit or living tree fragrance compositions of our invention and, if desired, one or more auxiliary perfume ingredients are useful, taken alone or in perfume compositions as olfactory components in anionic, cationic, nonionic or zwitterionic detergents, soaps, fabric softener compositions, fabric softener articles for use in clothes dryers (e.g., "BOUNCE®", a registered trademark of the Procter & Gamble Company of Cincinnati, Ohio), space odorants and deodorants, perfumes, colognes, toilet waters, bath preparations, such as lacquers, brilliantines, creams, deodorants, hand lotions and sun screens; powders such as talcs, dusting powders, face powders and the like.

When used as an olfactory component in perfume compositions or perfumed articles, such as anionic, cationic, nonionic, or zwitterionic detergents and fabric softener compositions and fabric softener articles (e.g., for use in clothing dryers) as little as 0.05% of at least one of the living flower, living leaf, living fruit or living tree fragrance compositions of our invention and, if desired, one or more auxiliary perfume ingredients will suffice to impart various floral or piney or eucalyptus aroma nuances. Generally, no more than 0.5% of at least one of the living flower, living leaf, living fruit or living tree perfume compositions of our invention and, if desired, one or more auxiliary perfume ingredients based on the ultimate end product is required in the perfumed article; however, the perfumed article can contain as much as 5% of such living flower, living leaf, living fruit or living tree composition.

In addition, the perfume composition or fragrance composition of our invention can contain a vehicle or carrier for at least one of the living flower, living leaf, living fruit or living tree perfume compositions of our invention and, if desired, one or more auxiliary perfume ingredients. The vehicle can be a liquid such as a non-toxic alcohol, a non-toxic glycol or the like. The carrier can also be an absorbent solid, such as a gum (e.g., gum arabic, xanthan gum or guar gum) or components for encapsulating the composition (such as gelatin as by means of coacervation).

It will thus be apparent that at least one of the living flower, living fruit, living leaf and/or living tree compositions of our invention and, if desired, one or more auxiliary perfume ingredients can be used to alter the sensory properties, particularly organoleptic properties of a wide variety of consumable materials.

BRIEF DESCRIPTION OF THE DRAWINGS

FIG. 1 is a cut-way side elevation view of one embodiment of the apparatus of our invention wherein two single totally enclosed 3-spaces are spherical in shape and each has contained therein a species of living flowers, the two species being different from one another. The headspace of each of the two living flowers is simultaneously trapped in a single trapping substance located in a single trapping tube-containing apparatus subcombination.

FIG. 1A is another embodiment of the apparatus of FIG. 1 showing the use of ultraviolet sources emitting ultraviolet radiation onto each of the two totally enclosed 3-spaces FIG. 1B is another embodiment of the apparatus of FIG. 1 showing the use of infrared sources emitting infrared radiation onto the living flowers contained within each of the two totally enclosed 3-spaces.

FIG. 1C is another embodiment of the apparatus of FIG. 1 showing the use of both ultraviolet sources and infrared sources emitting respectively, ultraviolet and infrared radiation onto the living flowers contained in each of the totally enclosed 3-spaces.

FIG. 1D is another embodiment of the apparatus of our invention showing a cut-away side elevation view of said apparatus wherein two totally enclosed 3-spaces are spherical in shape and each contains within the totally enclosed 3-space (1) in one totally enclosed 3-space a species of living flower; and (2) in the second totally enclosed 3-space a living leaf.

FIG. 1E is a cut-away side elevation view of an embodiment of the apparatus of our invention wherein two single totally enclosed 3-spaces are spherical in shape and each has contained therein a species of living leaf, the two species being different from one another. The headspace of each of the two living leaves ms simultaneously trapped in a single trapping substance located in a single trapping tube-containing apparatus subcombination.

FIG. 2 is a cut-away side elevation view of another embodiment of the apparatus of our invention wherein three single totally enclosed 3-spaces are spherical in shape and each has contained therein a species of living flowers, the three species of living flowers being different from one another. The headspace of each of the three living flowers is simultaneously trapped in a single trapping substance located in a single trapping tube-containing apparatus subcombination.

FIG. 3 is a cut-away side elevation view of another embodiment of the apparatus of our invention wherein four single totally enclosed 3-spaces are spherical in shape and each has contained therein a species of living flowers, the four species being different from one another. The headspace of each of the four living flowers is simultaneously trapped in a single trapping substance located in a single trapping tube-containing apparatus subcombination.

FIG. 8 is a cut-away side elevation view of another embodiment of the apparatus of our invention wherein three single totally enclosed 3-spaces are spherical in shape; the first totally enclosed 3-space contains a living leaf; the second totally enclosed 3-space contains a species of living flowers; the third totally enclosed 3-space contains a species of a living fruit. The headspace of each of the living leaf, the living flower and the living fruit are simultaneously trapped in a single trapping substance located in a single trapping tube-containing apparatus subcombination.

FIG. 8A shows the single trapping tube-containing apparatus subcombination used in the apparatus and in the process shown in FIG. 8.

FIG. 11 is the side elevation view of a part of the apparatus of our invention wherein a single totally enclosed 3-space is spherical in shape and has contained therein a species of living fruit.

FIG. 12 shows another view of the apparatus of FIG. 11 showing, via hidden line a living fruit enclosed within the apparatus portion.

FIG. 13 is a cut-away side elevation view of the apparatus of FIG. 12 taken along lines 13—13 showing in perspective view the living fruit contained in the apparatus.

FIG. 14 is a perspective view of an analytical volatile substance trapping apparatus subcombination comprising a hollow substantially cylindrical key tube, and a trapping cylinder contained partially within the key tube; with four hollow cylindrical feeding tubes extending in diverse directions away from the key tube upper rim with each of the feeding tubes affixed at a common hollow totally enclosed volumetric mixing junction to the upper rim of the key tube.

FIG. 15 is a top view of the apparatus subcombination of FIG. 14.

FIG. 16 is a cut-away side elevation view of the apparatus of FIG. 14.

FIG. 17 is a perspective view of another embodiment of the analytical volatile substance trapping apparatus subcombination of our invention comprising a hollow substantially cylindrical key tube; a trapping cylinder contained partially within the key tube; and communicating with and jointly and sealably affixed at a common hollow totally enclosed volumetric mixing junction to the upper rim of the key tube four hollow substantially cylindrical feeding tubes extending in diverse directions away from the key tube. The apparatus is useful in carrying out the process and being used in the apparatus shown in FIG. 3.

FIG. 18 is a cut-away side elevation view of the apparatus of FIG. 17.

FIG. 19 is a top view of the apparatus of FIG. 17.

FIG. 20 is a GC-mass spectrum of the constitution of a composition evolved from two living flowers using the apparatus of FIG. 1; the Dwarf Navel Orange Flower and the Jasmin Nitidum Flower.

DETAILED DESCRIPTION OF THE DRAWINGS

Figure 4:
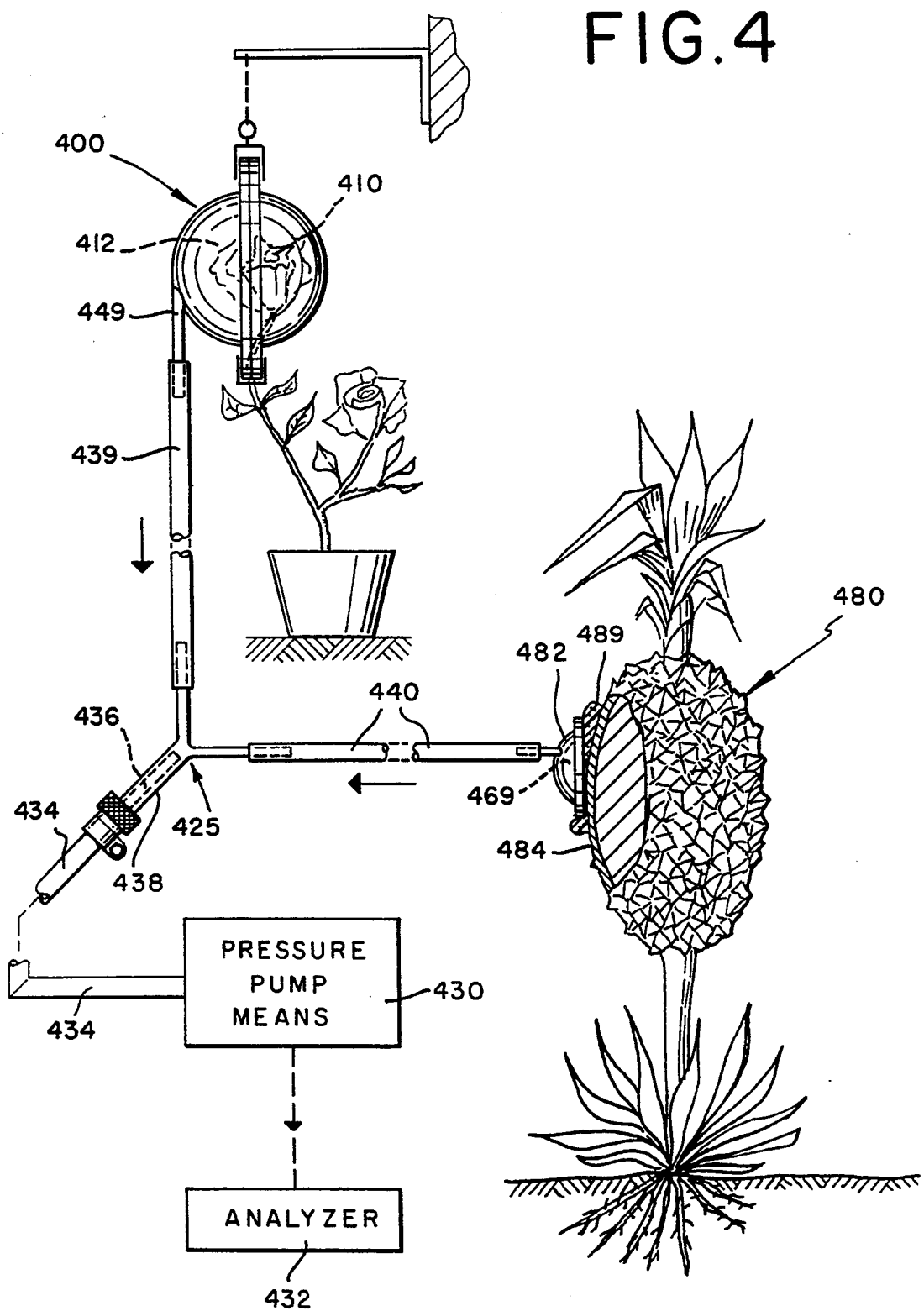
FIG. 4 is a cut-away side elevation view of another embodiment of the apparatus of our invention wherein a single totally enclosed 3-space is spherical in shape and has contained therein a species of living flower; and a enclosed 3-space covers a part of a surface of a living pineapple. The headspace of the living pineapple surface and the headspace of the living flower are simultaneously trapped in a single trapping substance located in a single trapping tube-containing apparatus subcombination.

FIGS. 1, 1A, 1B, 1C, 1D, 1E, 2, 3, 4, 5, 6, 7, 8, 9 and 10 set forth apparatus for qualitatively and quantitatively analyzing the emitted aroma and rates of emission of the aroma components thereof from two or more living flowers, living fruits, living leaves, partial surfaces of living fruits and partial bark surfaces of living trees using individual enclosed 3-spaces for each living flower, living fruit, living leaf or partial section of living fruit or living tree bark and using a single aroma headspace trapping apparatus subcombination containing a single headspace trapping substance.

More specifically, FIG. 1 is a cut-away side elevation view of one embodiment of the apparatus of our invention wherein two single totally enclosed 3-spaces, 100 and 102 are spherical in shape and each has contained therein a species of living flowers, living flower 108 in enclosed space 102 living flower 110 in enclosed space 100. The two species of living flower 108 and 110 are different from one another. The headspace of each of the two living flowers, 112 for flower 110 and 114 for flower 108 are simultaneously trapped in a single trapping substance 136 located in a single trapping tube-containing apparatus 125 subcombination. Apparatus subcombination 125 consists of key tube 138 and trapping tube 134 holding trapping substance 136 therein. The trapping tube 134 is connected to a vacuum pressure pump means 130 which is further connected to a headspace analytical device, e.g., a GC-mass spectrum analysis apparatus 132. Analysis apparatus 132 may also include nuclear magnetic spectrum analysis apparatus. Apparatus subcombination 125 is connected to enclosed 3-space 100 via feeding tube 139 and is connected to enclosed space 102 via feeding tube 140. Enclosed headspace 100 contains two hemispherical parts connected together said parts indicated by reference numeral 104 (for flower 110) and by reference numeral 106 (for flower 108). Enclosed 3-space 100 contains fritted air openings 113 for permitting a velocity of air flow to pass past flower 110.

FIG. 1A sets forth a variation of the apparatus of FIG. 1 showing the use of ultraviolet light imparting radiation devices 190a (for flower 110) and 190b (for flower 108) with the ultraviolet radiation shown by reference numeral 191a (for device 190a) and by 191b (for device 190b).

FIG. 1B shows another variation of the apparatus of FIG. 1 wherein infrared radiation apparatus 192a impinges infrared radiation 193a onto flower 110 and infrared inducing apparatus 192b impinges infrared radiation 193b onto flower 108.

FIG. 1C is another variation of the apparatus of our invention wherein ultraviolet-radiating apparatus 190a radiates ultraviolet radiation 191a and infrared-radiating apparatus 192a radiates infrared radiation 193a into enclosure 100; and ultraviolet radiating apparatus 190b radiates ultraviolet radiation 191b and infrared radiating apparatus 192b radiates infrared radiation 193b into enclosed 3-space 102.

FIG. 1D also sets forth the apparatus of FIG. 1 showing in one spherical enclosure 100d a living leaf 160 connected via stem 165 to plant 166 contained in ground 167 and in enclosed 3-space 102d living flower 108 connected via stem 118 to plant 119 growing in ground 120.

FIG. 1E sets forth another variation of the apparatus of FIG. 1 showing in enclosure 100e living leaf 160 connected via stem 165 to plant 166 growing in ground 167; and living leaf 168 contained in enclosure 102e growing via stem 178 attached to plant 179 in ground 120.

FIG. 2 sets forth another variation of the apparatus of our invention. Three living flowers are contained in three separate enclosed 3-spaces with each headspace connected to a single headspace trapping apparatus subcombination containing headspace trapping substance.

Thus, living flower 1210 connected through stem 1215 implant 1216 located in ground 1217 emits aromatizing materials into headspace 1212. Simultaneously, living flower 1208 connected to plant 1219 via stem 1218, said plant growing in ground 1220 emits aromatizing materials into headspace 1214. Living flower 1253 connected via stem 1258 to living plant 1259 growing in ground 1260 emits aromatizing substances into headspace 1254. The enclosure for living flower 1214 is indicated by reference numeral 1202 and that enclosure is fabricated from hemispherical shells 1206. The enclosure for living flower 1253 is indicated by reference numeral 1250 and that enclosure is fabricated from hemispherical shells 1252.

Aromatizing substance from headspace 1212, from headspace 1254 and from headspace 1214 pass through feeding tubes, respectively, 1239, 1262 and 1240 into trapping substance 1236 contained in headspace trapping apparatus subcombination 1225 which includes key tube 1238. Pressure pump means 1230 via vacuum pumping causes air to flow through fritted glass openings 1213 (in enclosures 1200 and 1202) past living flowers 1210 and 1208 through feeding tubes 1239 and 1240 into headspace trapping apparatus subcombination 1225. Subsequently, the trapping substance 1236 which traps the headspace components is then removed from the apparatus extracted and analyzed using analyzer 1232.

FIG. 3 sets forth apparatus similar to that of FIG. 2 with the exception that four single totally enclosed 3-spaces contain four separate living flowers. Headspace from enclosure 300 feeds through feeding line 339 into headspace trapping apparatus 25 onto headspace trapping substance 336. Simultaneously headspace from enclosure 302 feeds through feeding line 340 into headspace trapping apparatus 325; headspace from apparatus 370 feeds through feed line 372 into headspace trapping apparatus 325; and headspace from apparatus 350 feed through feed line 362 into headspace trapping apparatus 325 onto headspace trapping substance 336. Each of the headspaces is caused to be trapped in headspace trapping apparatus 325 by means of the use of vacuum pressure pump means 330 via vacuum line 334. The headspace trapped on headspace trapping substance 336 is then removed therefrom and analyzed using analyzer 332.

Referring to FIG. 4, FIG. 4 is a cut-away side elevation view of another embodiment of the apparatus of our invention wherein one totally enclosed 3-space 400 is spherical in shape and contains therein a species of living flower 410 with headspace 412. Another enclosed 3-space 482 covers in part the surface of living pineapple 480 and enclosure 482 is sealed at its circumference using sealant 489. The headspace of enclosure 482 is indicated by reference numeral 469. When vacuum pressure pump means 430 is engaged, headspace from 410 and from 469 is simultaneously fed into headspace trapping apparatus subcombination 25 containing headspace trapping substance 436. The headspace 412 is drawn through tube 449 and then through feeding tube 439 into headspace trapping substance 436 surrounded by key tube 438. The headspace 469 is drawn using vacuum pump 430 through feeding tube 440 into headspace trapping apparatus 425 and onto headspace trapping substance 436. The vacuum pump is connected to headspace trapping apparatus subcombination 425 via line 434. After the headspace aromatizing substances are trapped on trapping substance 436, the trapping substance is removed and extracted and then analyzed using analyzer 432.

Figure 5:
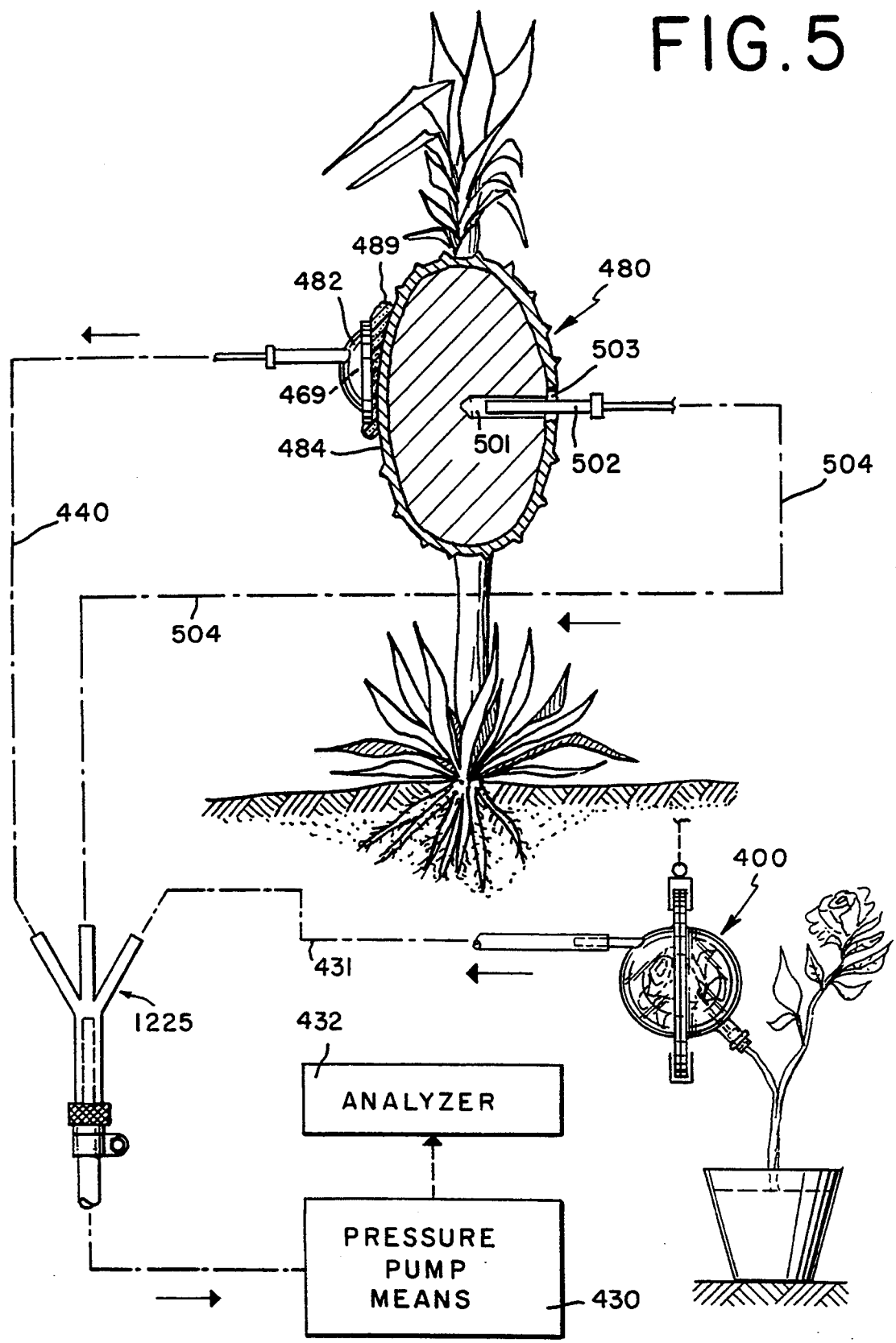
FIG. 5 is a cut-away side elevation view of another embodiment of the apparatus of our invention wherein a single totally enclosed 3-space is spherical in shape and has contained within a species of living flower; a second enclosed 3-space covers a portion of a surface of a living pineapple; and a headspace capturing device is inserted into the inner part of said living pineapple. The headspace of said living flower, the portion of the surface of the living pineapple as well as the inner part of the living pineapple are all simultaneously trapped in a single trapping substance located in a single trapping tube-containing apparatus subcombination

FIG. 5 shows another embodiment of the apparatus of our invention wherein a single totally enclosed 3-space 400 contains a living flower; an enclosed 3-space 482 covers portion of the surface of a living pineapple 480; and headspace trapping device 502 is contained in core 501 of the living pineapple 8 through opening 503 of the living pineapple 480. When vacuum pressure pump means 430 is engaged, headspace from enclosure 400 is passed through line 431; headspace from core is passed through line 504; and headspace 469 from the surface of pineapple 480, from enclosure 482 is passed through 440 all simultaneously into headspace trapping apparatus subcombination 1225. After the three headspace aromatizing substance combinations are collected in headspace trapping apparatus subcombination 1225, they are removed therefrom and analyzed in analyzer 432.

Figure 6:
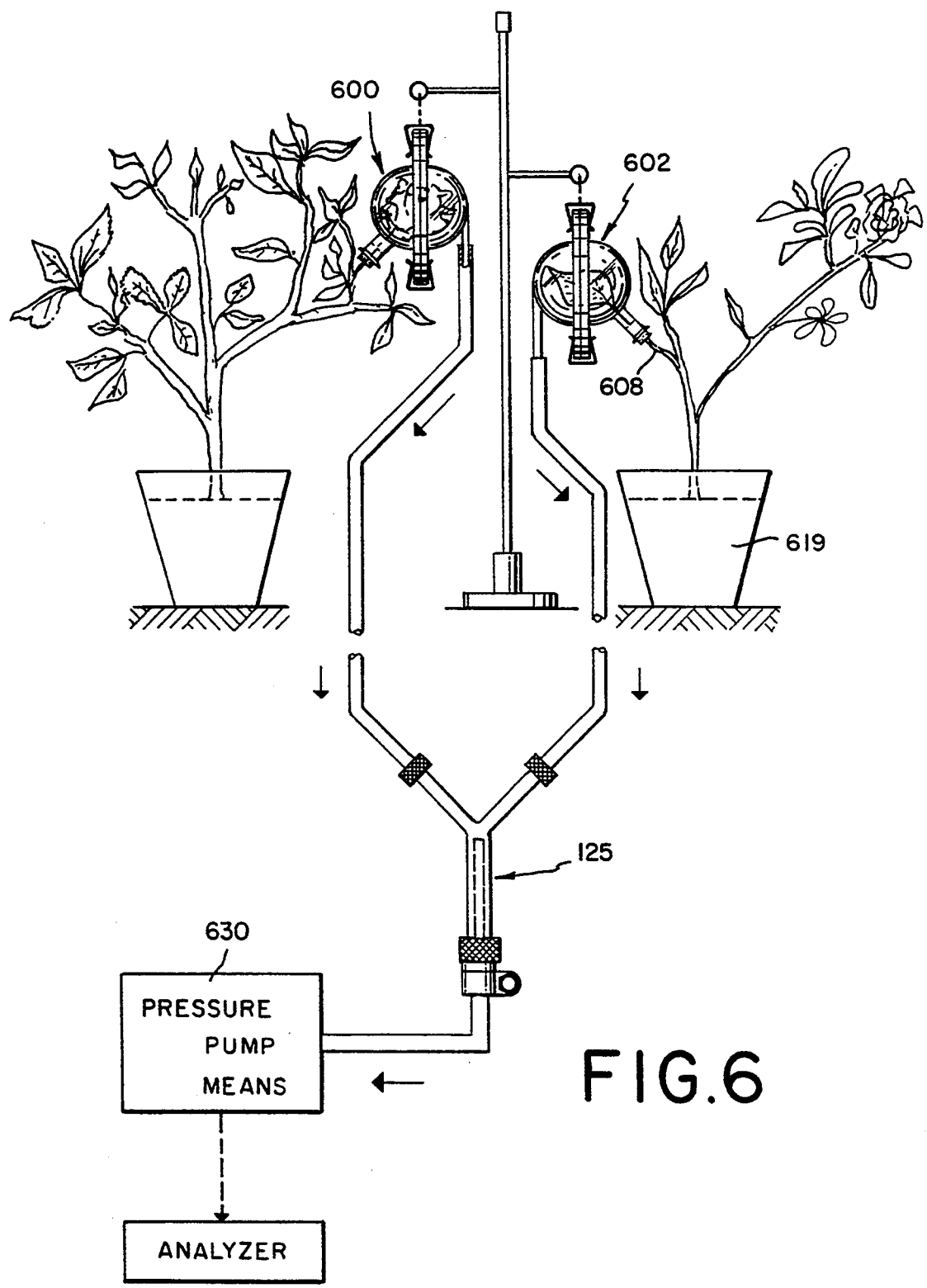
FIG. 6 is a cut-away side elevation view of another embodiment of the apparatus of our invention wherein two single totally enclosed 3-spaces are spherical in shape; with one enclosed 3-space containing therein a species of living flower and the second of the enclosed 3-spaces containing a species of living leaf. The headspace of the living leaf and the headsapce of the living flower are each simultaneously rapped in a single trapping substance located in a single trapping tube-containing apparatus subcombination.

FIG. 6 is a cut-away side elevation view of another embodiment of the apparatus of our invention wherein two single totally enclosed 3-spaces 600 and 602 are spherical in shape. Enclosure 600 contains a living flower and enclosure 602 contains a living leaf connected via stem 608 to a plant growing in ground 619. The headspaces from enclosure 600 and 602 pass through feeding tubes to headspace collection apparatus subcombination 625 when vacuum pressure pump means 630 is applied to the system. After the headspace from the living flower from enclosure 600 and from the living leaf from enclosure 602 are collected in collection apparatus subcombination 125 they are removed from the trapping substance therein and analyzed using the analyzer shown in FIG. 6.

Figure 7:
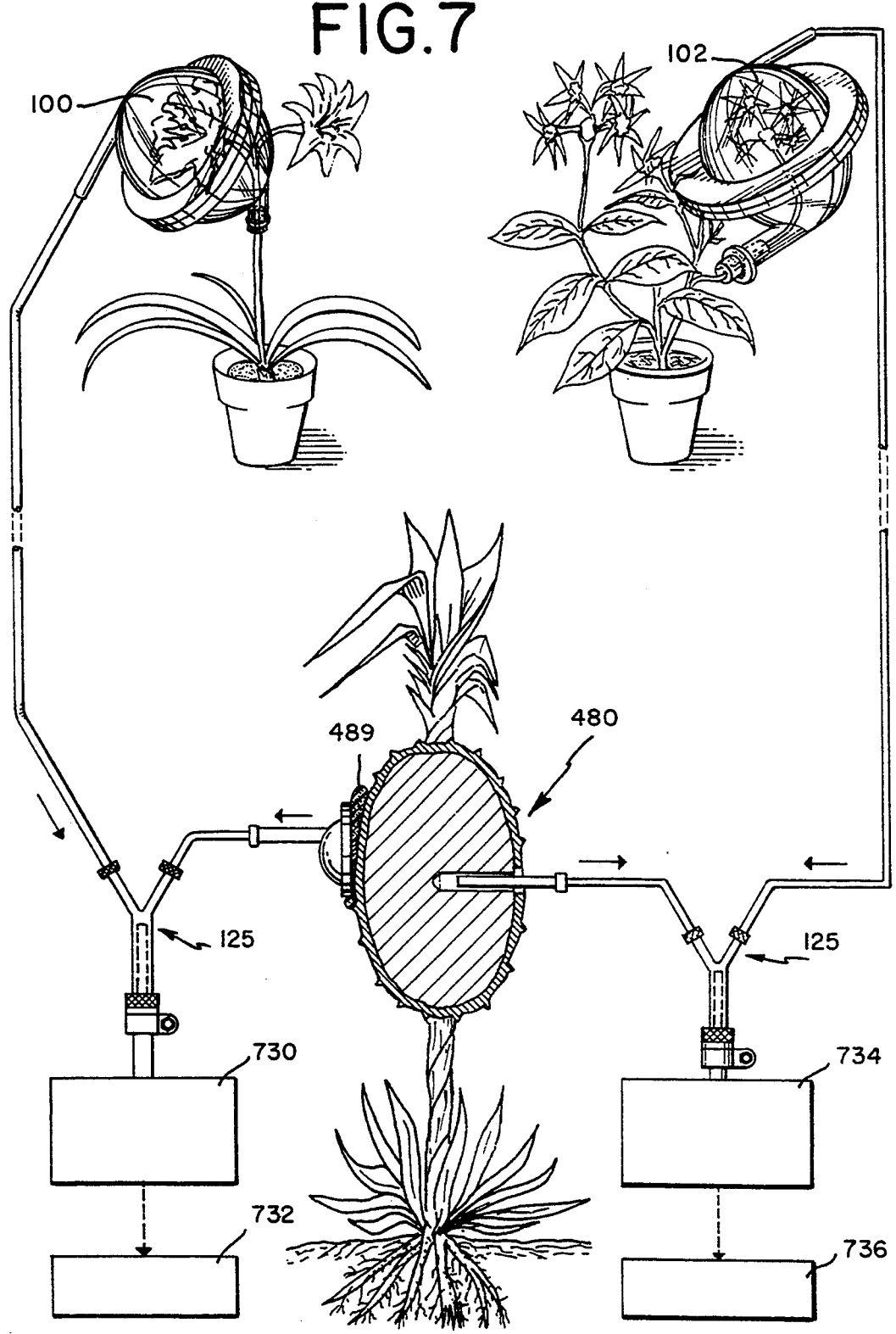
FIG. 7 is a cut-away side elevation view of another embodiment of the apparatus of our invention wherein two single totally enclosed 3-spaces are spherical in shape and each has contained therein a species of living flowers, the two species being different from one another. In addition, another totally enclosed 3-space covers a portion of a living pineapple. In addition, a headspace capturing device is contained within the inner part of said living pineapple. The headspace of the living flower and the portion of the surface of the living pineapple are simultaneously entrapped in a first single trapping substance located in a single trapping tube-containing apparatus subcombination. The headspace of the second living flower and the headspace of the inner part of said living pineapple are also simultaneously entrapped in a second single trapping substance located in a second single trapping tube apparatus subcombination.

FIG. 7 is cut-away side elevation view of another embodiment of the apparatus of our invention wherein two single totally enclosed 3-spaces 100 and 102 are spherical in and each contains therein two different species of living flowers. Another enclosure surrounds part of the surface of living pineapple 480 sealed thereto at 489. In addition, a headspace trapping device is inserted into the inner part of living pineapple 480. Headspace from the inner part of living pineapple 480 and from enclosure 402 is simultaneously trapped in headspace trapping apparatus subcombination 125 when vacuum from vacuum pump 734 is applied. Headspace from enclosure 102 and from part of the surface of living pineapple 480 is simultaneously trapped in another headspace trapping apparatus subcombination 125 when vacuum from vacuum apparatus 730 is applied to the apparatus 125. Headspace using pump 730 analyzed via analyzer 732. Headspace using pump 734 is analyzed using analyzer 736.

Referring to FIG. 8, FIG. 8 is a cut-away side elevation view of another embodiment of the apparatus of put invention wherein three single totally enclosed 3-spaces, 800, 802 and 804 are spherical in shape. Enclosure 800 contains living leaf 810. Enclosure 802 contains living flower species 808. Enclosure 804 contains living fruit 820 connected living tree 880. Enclosure 804 contains headspace 824. Headspace 824 together with the headspace from enclosure 802 and the headspace from enclosure 800 passes through feeding tubes simultaneously into headspace trapping apparatus subcombination 225 containing headspace trapping substance as a result of engagement of vacuum pump apparatus 830. The headspace trapping apparatus 225 is shown in detail in FIG. 8A. Thus in FIG. 8A, the headspace trapping apparatus 225 consists of key tube 238 which encloses headspace trapping substance 237 contained in inner tube 236. Key tube 238 it its upper rim is connected simultaneously to feeding tube 239 (from enclosure 800); feeding tube 262 (from enclosure 802) and feeding tube 240 (from enclosure 804) at volumetric junction 239a. At the end of the collection of the headspace on headspace trapping substance 237, headspace trapping substance 237 is removed and the headspace aromatizing substances are extracted therefrom and subsequently analyzed using analyzer 832.

Figure 9:
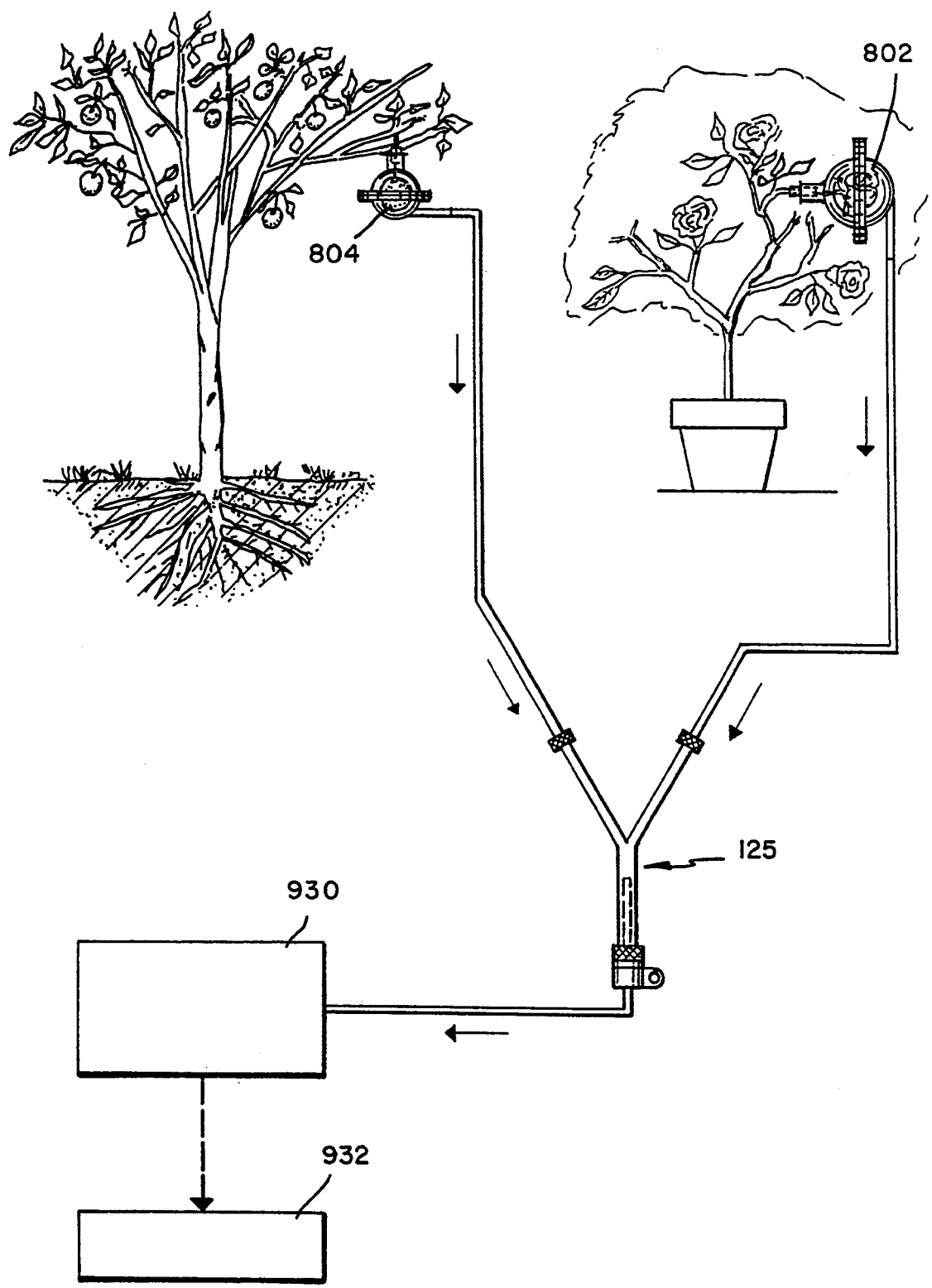
FIG. 9 is a cut-away side elevation view of another embodiment of the apparatus of our invention wherein two single totally enclosed 3-spaces are spherical in shape. The first totally enclosed 3-space contains a species of living flower. The second totally enclosed 3-space contains a species of living fruit. The headspace of each of the living fruit and of the living flower are simultaneously trapped in a single trapping substance located in a single trapping tube-contain apparatus subcombination.

FIG. 9 is a cut-away side elevation view of another embodiment of the apparatus of our invention wherein two single totally enclosed 3-spaces 802 and 804 are spherical in shape. 3-Space 802 contains a living flower and 3-space 804 contains a living fruit. The headspaces from 3-space 802 and 3-space 804 feed through feeding lines into headspace collection apparatus 125 where, simultaneously, the head spaces from enclosure 802 and 804 are trapped on headspace collection substance when vacuum pump 930 is engaged. After the headspace substance is trapped in headspace apparatus subcombination 125 the headspace collection substance is removed therefrom, extracted and analyzed using analyzing apparatus 932.

Figure 10:
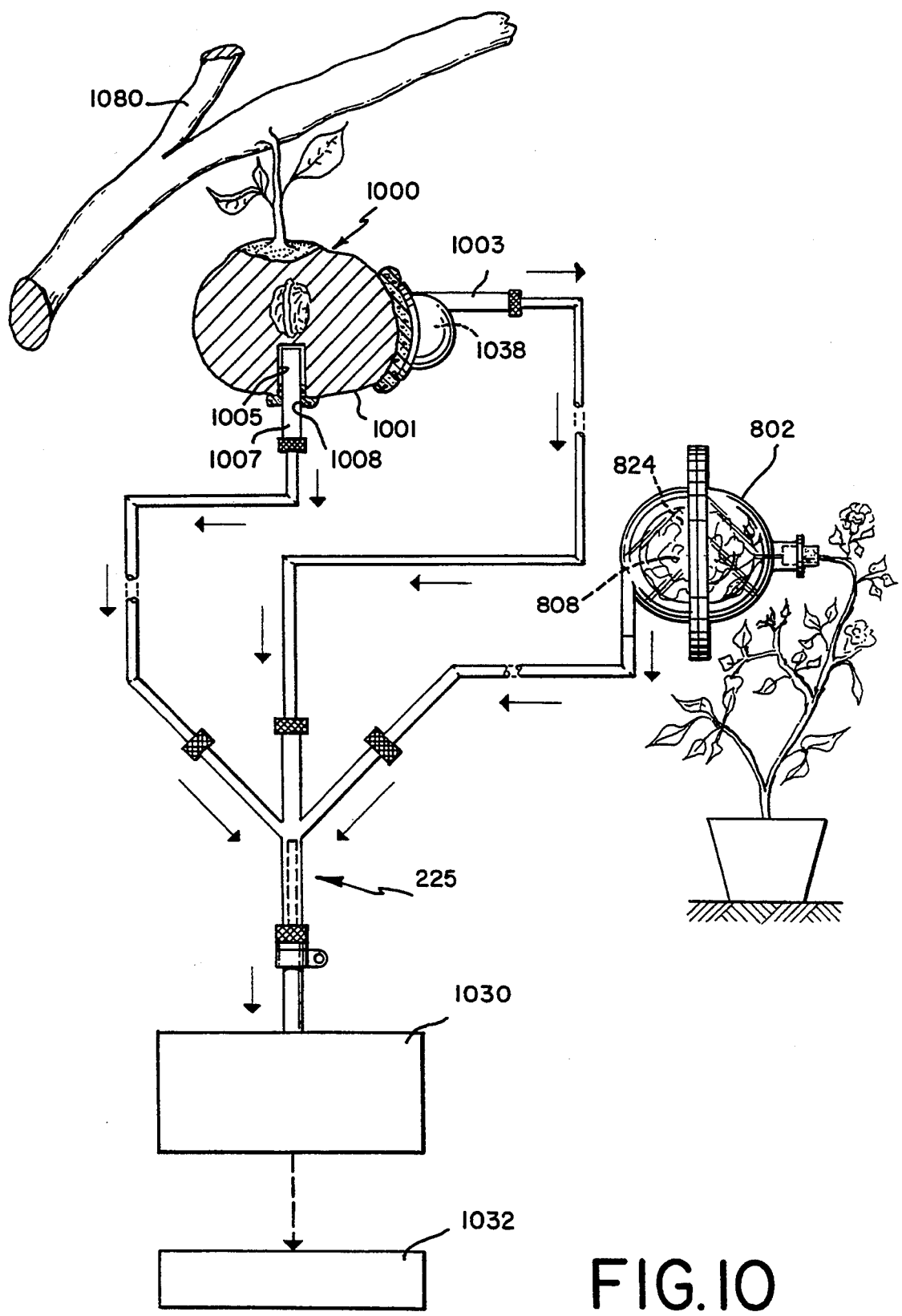
FIG. 10 is a cut-away side elevation view of another embodiment of the apparatus of our invention wherein a single totally enclosed 3-space is spherical in shape and has contained therein a species of living flower; and another enclosed headspace covers a part of the surface of a living peach connected via a stem to a peach tree branch; and a headspace trapping device is inserted into said living peach. The headspace of each of the living flower; the part of the surface of the living peach; and the inner part of the living peach are each simultaneously trapped in a single trapping substance located in a single trapping tube-containing apparatus subcombination.

FIG. 10 is a cut-away side elevation view of another embodiment of the apparatus of our invention wherein a single totally enclosed 3-space 802 is spherical in shape and contains therein a species of living flower 808. Above the living flower is headspace 824. In addition, the apparatus embodiment of FIG. 10 contains an enclosure covering a part of the surface 1001 of peach 1000 connected to branch of peach tree 1080. The enclosure has headspace 1038 connected via tube 1003 to headspace trapping apparatus subcombination 225. In addition, headspace collection device 1007 is introduced into core 1008 internally to peach 1000 through opening 1008.

Headspace from core 1005, from enclosure headspace 1038, and 824 is simultaneously collected in headspace trapping apparatus subcombination 225 on engagement of vacuum pump 1030.

After collection of the headspace in headspace collection apparatus subcombination 25, the headspace collection substance is removed therefrom, extracted and analyzed using analyzer 1032.

FIGS. 11, 12 and 13 show detailed views of enclosures of the apparatus of our invention containing a living fruit 820. The living fruit 820 in FIGS. 11, 12 and 13 is contained in enclosure 1100 which consists of two hemispherical sides 1100a and 1100b clamped together using clamps 1108. The living fruit 820 is contained in enclosure 1100 through its stem which is in place at opening 1102. The stem is held in place using stopper 1126 at the junction of the two hemispherical portions, said junction being indicated by reference numeral 1120. The two hemispherical portions 1100a and 1100b are clamped by clamps 1108 at locations 1106a, 1106b and 1106c with the clamps being maintained in place as a result of each hemispherical portion 1100a and 1100b having lip 1104 surrounding hemispherical edge 1122. On engagement of the vacuum pump, air flows as indicated by reference numeral 1128 through headspace 824 and then through tube 1101 and then through feeding tube 1130 into headspace collection apparatus subcombination attached no feeding tube 1130.

FIGS. 14, 15 and 16 set forth an embodiment of the headspace collection apparatus subcombination as claimed in claim 2 and as shown in use in FIG. 3. Thus, FIGS. 14, 15 and 16 show an analytical volatile substance trapping apparatus subcombination consisting of:

(x) a hollow substantially cylindrical key tube 338 having an internal key tube diameter and a key tube length; and having an upper key tube opening having an upper substantially circular rim and a lower key tube opening having a lower substantially circular rim;

(y) a trapping cylinder 336 contained partially within key tube 338 extending substantially beyond said lower key tube opening and substantially concentric with said key tube 338, said trapping cylinder 336 consisting of a hollow cylindrical tube containing a trapping material 337 for trapping volatiles; said trapping cylinder 336 having an outer trapping tube diameter substantially less than he inner diameter of said key tube, the space between the key tube and the trapping cylinder 336 being sealed in gas tight fashion; and (z) communicating with and jointly and sealably affixed at a common hollow totally enclosed volumetric mixing junction 339 to the said upper rim of said upper opening of said key tube 338, a plurality of hollow substantially cylindrical feeding tubes (four in number)(362, 330, 340 and 372) extending in diverse directions away from said key tube upper rim, each of said feeding tubes 330, 340, 362 and 372 having an outer substantially circular feeding tube rim and a lower substantially circular feeding tube rim said lower feeding tube rim being sealably affixed an communicating with said volumetric mixing junction 339, such that a continuous unbroken travel path for molecules of volatiles exist from each of said outer feeding tube rims 330, 362, 340 and 372 o he said lower rim of said trapping cylinder 336. The overall apparatus is indicated by reference numeral 325.

FIGS. 17, 18 and 19 illustrate another embodiment of the analytical volatile substance trapping apparatus subcombination of our invention consisting of:

(x) a hollow substantially cylindrical key tube 1740 having an internal key tube diameter and a key length; and having an upper key tube opening having an upper substantially circular rim and a lower key tube opening having a lower substantially circular rim;

(y) a trapping cylinder 1736 contained partially within said key tube 1740, extending substantially beyond said lower key tube opening and substantially concentric with said key tube, said trapping cylinder 1736 consisting of a hollow cylindrical tube containing trapping material 1737 for trapping volatiles; said trapping cylinder 1736 having an outer trapping tube diameter substantially less than the inner diameter of said key tube 1740, he space between the key tube 1740 and the trapping cylinder 1736 being sealed in gas tight fashion; and (z) communicating with and jointly and sealably affixed at a common hollow totally enclosed volumetric mixing junction 1739 to the said upper rim of said upper opening of said key tube, four hollow substantially cylindrical feeding tubes 1701a, 1701b, 1701c an 1701d extending in diverse directions away from said key tube upper rim, each of said feeding tubes 1701a, 1701b, 1701c and 1701d having an outer substantially circular feeding tube rim and a lower substantially circular feeding tube rim said lower feeding tube rim being sealably affixed and communicating with said volumetric mixing junction 1739, such that a continuous unbroken travel path for molecules of volatiles exist from each of said outer feeding the rims to the said lower rim of said trapping cylinder 1736 whereby volatiles pass through said feeding tube 1701a, 1701b, 1701c and 1701d in a direction towards said key tube 1740 and are entrapped in said trapping materials 1737 located in said trapping tube 1736. The key tube 1740, in the apparatus of FIGS. 17, 18 and 19 is held in place in connecting block 1749 which surrounds the volumetric junction 1739 and holds in place a filtering screen (for filtering small dust particles) 1750. The connecting block 1749 is held in place with a locking nut. The overall apparatus is indicated by reference numeral 1700.

Figure 24:
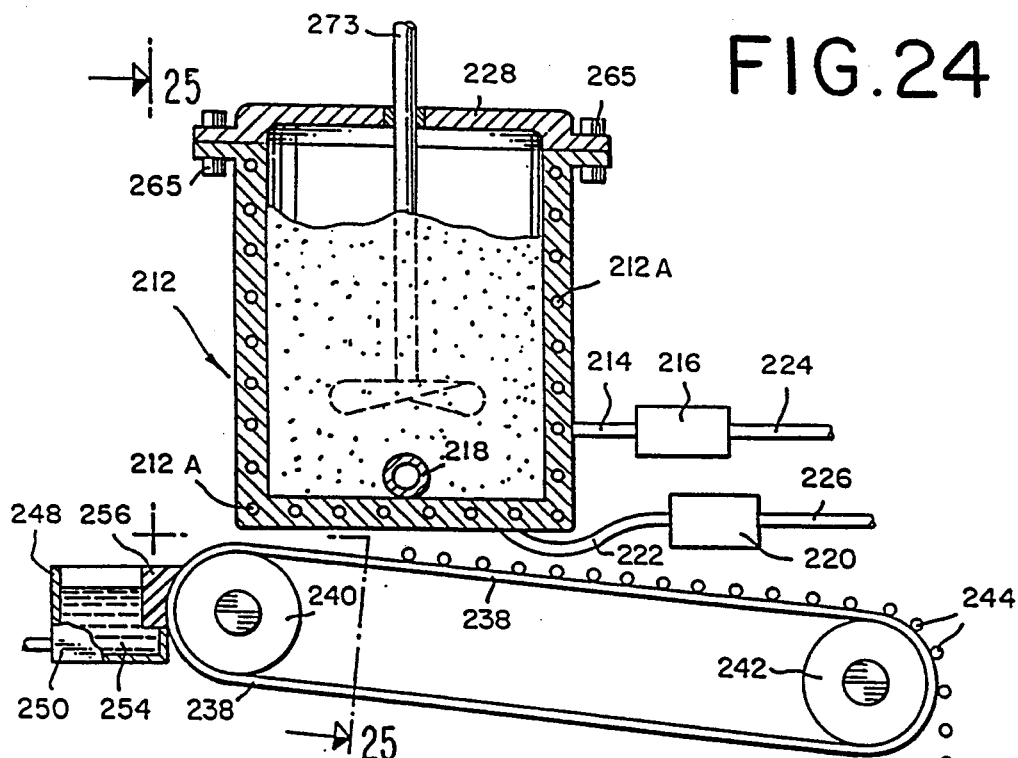
FIG. 24 represents a cut-away side elevation view of apparatus used in forming perfumed polymers containing at least one of the living flower, living fruit, living leaf and/or living tree compositions of our invention.
Figure 25:
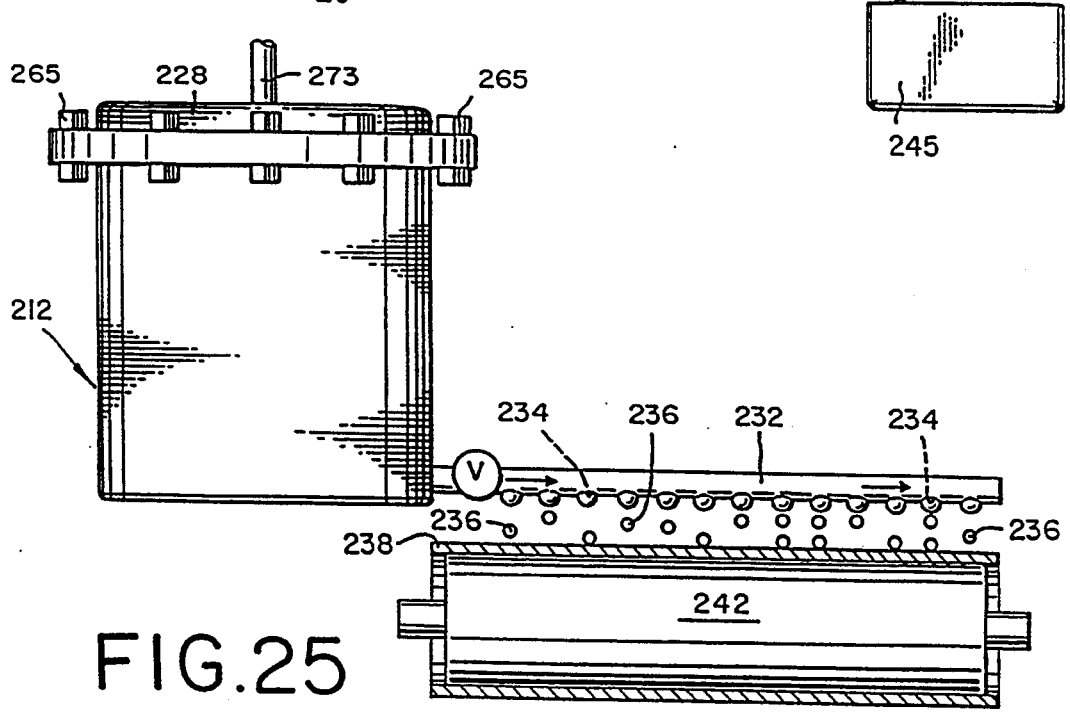
FIG. 25 is a front view of the apparatus of FIG. 24 looking in the direction of the arrows.

Referring to FIGS. 24 and 25, there is provided a process for forming scented polymer pellets (wherein the polymer nay be a thermoplastic polymer such as low density polyethylene polypropylene or copolymers of ethylene-vinyl acetate or mixtures of a polymer and copolymer such as a copolymer of ethylene-vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower-most portion of container is maintained at a slightly lower temperature and the material of the container is taken off at such location delivery through the conduit. Thus, referring to FIGS. 24 and 25, in particular, the apparatus used in producing such elements comprises a device for forming the polymer containing perfume, e.g., polyethylene or polyethylene-polyvinyl acetate or mixtures of same or polypropylene, or the like, which comprises a vat or container 212 into which the polymer taken alone or in admixture with other copolymers and a perfume substance containing at least one of the living flower, living fruit, living tree and/or living leaf fragrances of our invention is placed. The container is closed by means of an air-tight lid 228 and clamped to the container by bolts 265. A stirrer 273 traverses the lid or cover 228 in an air-tight manner and is rotatable in a suitable manner.

A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds.

Heating means (coils 212A) are operated to maintain he upper portion of the container 212 within a temperature range of, for example, 250°–260° C. in the case of low density polyethylene. The bottom portion of the container 212 is also heated by means of heating coils 212A regulated through the control 220 connected thereto through a connecting wire 222 to maintain the lower portion of the container 212 with a temperature range of 225°–240° C.

Thus, the polymer or mixture of polymers added to the container 212 is heated from 10–12 hours, whereafter the perfume composition or perfume material containing at least one of the living flower, living tree, living fruit and/or living leaf fragrances of our invention is quickly added to the melt. Generally, about 10–45 percent by weight of the resulting mixture of the perfumery substance is added to the polymer.

After the perfume material containing a least one of the living flower, living fruit, living tree and/or living leaf fragrances of our invention is added to the container 212 the mixture is stirred for a few minutes, for example, 5–15 minutes and maintained within the temperature ranges indicated previously by the heating coils 212A. The controls 216 and 220 are connected through cables 224 and 226 to a suitable supply of electric current for supplying the power for heating purposes.

Thereafter, the valve "V" is opened permitting the mass to flow outwardly through conduit 232 (also indicated by reference numeral 218 in FIG. 24) having a multiplicity of orifices 234 adjacent to the lower side thereof. The outer end of the conduit 232 is closed so that the liquid polymer intimately admixed with at least one of the living flower, living fruit, living tree and/or living leaf fragrances of our invention will continuously drop through the orifices 234 downwardly from the conduit 232. During this time, the temperature of the polymer intimately admixed with the perfumery substance in the container 212 is accurately controlled so that a temperature in the range of from about 240°–250° C. (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance containing at least one of the living flower, living fruit, living tree and/or living leaf fragrances of our invention through the orifices 234 at a rate which will insure the formation of droplets 236 which will fall downwardly onto a moving conveyor belt 238 caused no run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for formation of other functional products, e.g., garbage bags and the like.

The following examples are illustrative of processes for using the apparatus of our invention, processes for carrying out production of fragrance formulations of our invention and processes for using the living flower, living fruit, living tree and living leaf fragrances of our invention. These examples are illustrative and the invention is to be considered to be restricted thereto only as indicated in the appended claims.

All parts and percentages given herein are by weight unless otherwise specified.

EXAMPLE I

Analysis and Fragrance Preparation of Biflower Fragrance Using the Dwarf Navel Orange Flower and the Jasmin Nitidum Flower Apparatus was built as set forth in FIG. 1. The apparatus enclosures 100 and 102 each consists of two hemispherical shells fabricated from glass, having a shell wall 0.125" in thickness; and a shell diameter of 8". Prior to putting the hemispheric walls of shells 104 and shells 106 together, two living growing flowers; jasminum nitidum and dwarf navel orange flower (108 and 110 respectively) are placed through appropriate openings in apparatus 102 and 104, respectively. Thus, the flower 110 having stem 115 coming out of plant 116 is pushed through an opening of apparatus 100. The jasminum nitidum flower 108 is pushed through an opening of apparatus 102. Flower 108 is connected through stem 118 to plant 119. In each of apparatus enclosures 100 and 102 he two hemispheres are wedged together held in place by clamps.

Pump 130 is engaged and run for a period of two hours.

The aroma components of the combined flower headspace is trapped in a ⅛" diameter×4" long TENAX®-GC headspace trap further inserted into a glass tube being 5" in length×¼" outside diameter. The pump is an alpha-2 pump (vacuum pump), a "low flow" pump marketed by the Amatec Company of Largo, Florida 34643 (the "Amatec Constant Flow Sampler").

The analysis of the headspace is set forth in the GC-mass spectrum of FIG. 20.

The major components of the GC-mass spectrum of FIG. 20 are then obtained and admixed and these components are as follows:

| Ingredients | Parts by Weight |
| --- | --- |
| Myrcene | 1.25 |
| 2-Cyanobutane | 10.64 |
| Benzyl alcohol | 2.50 |
| Limonene | 1.25 |
| Trans-beta-ocimene | 2.15 |
| Methyl benzoate | 4.64 |
| Linalool | 12.52 |
| Beta-phenylethyl alcohol | 2.45 |
| Methyl salicylate | 3.62 |
| Methyl anthranilate | 1.05 |
| Cis-jasmone | 14.25 |
| Beta-caryophyllene | 1.05 |
| Beta-selinene | 4.12 |
| Alpha-farnesene | 8.13 |

The resulting fragrance can be described as having a floral aroma with orange flower and green topnotes and green and jasmine undertones.

EXAMPLE II

Analyses and Fragrance Preparation Using as the "Biflower", the Red Rose All That Jazz and the White Ginger Lily Flower A procedure was carried out identical to that of Example I with the exception that the two flowers contained in the headspace of the totally enclosed 3-space are the (i) red rose all that jazz and (ii) the white ginger lily flower.

Figure 21:
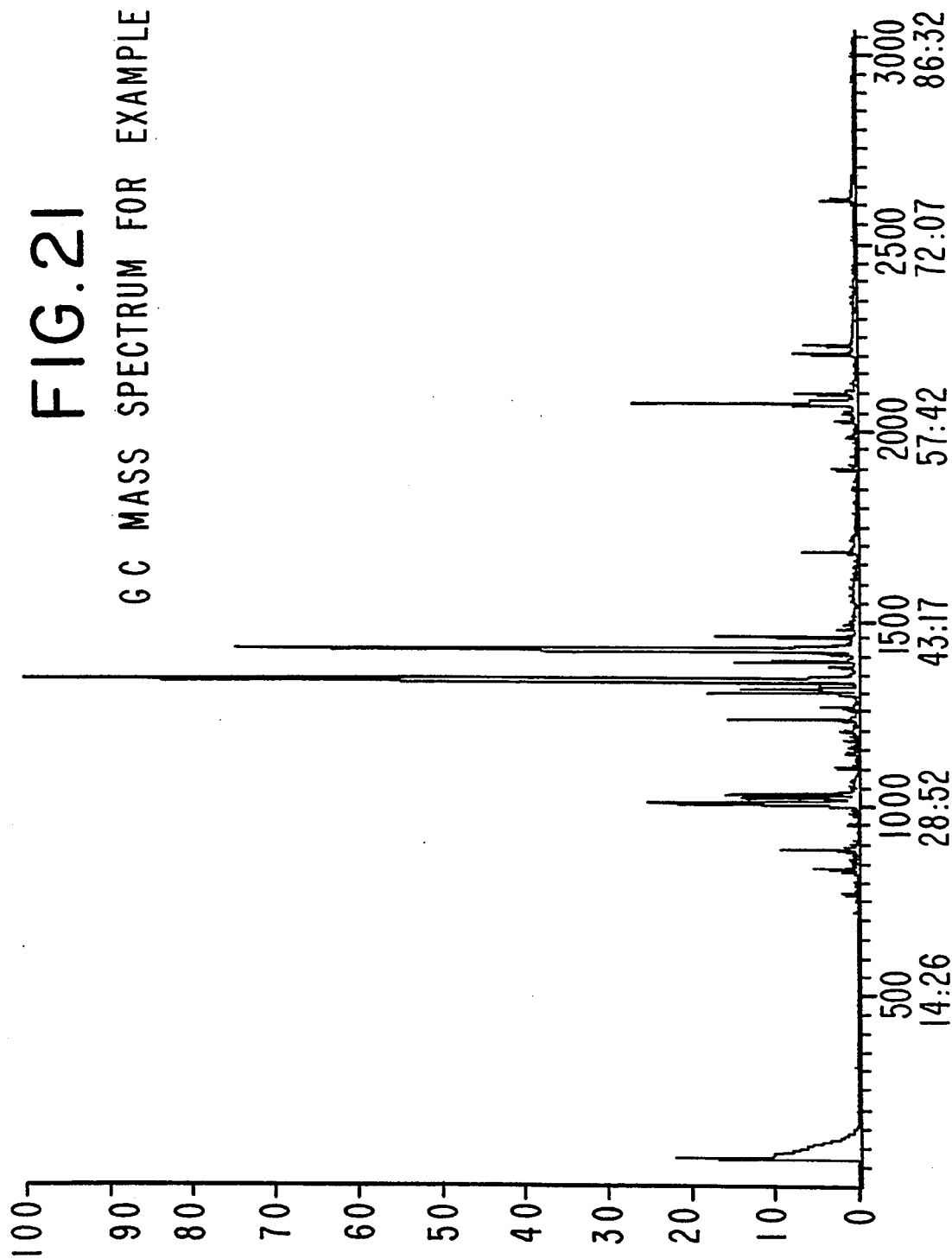
FIG. 21 is a GC-mass spectrum for the components of the aroma composition evolved using the apparatus of FIG. 1 from the two living flowers; The Red Rose All That Jazz and the White Ginger Lily Flower in accordance with the procedure of Example II.
Figure 22:
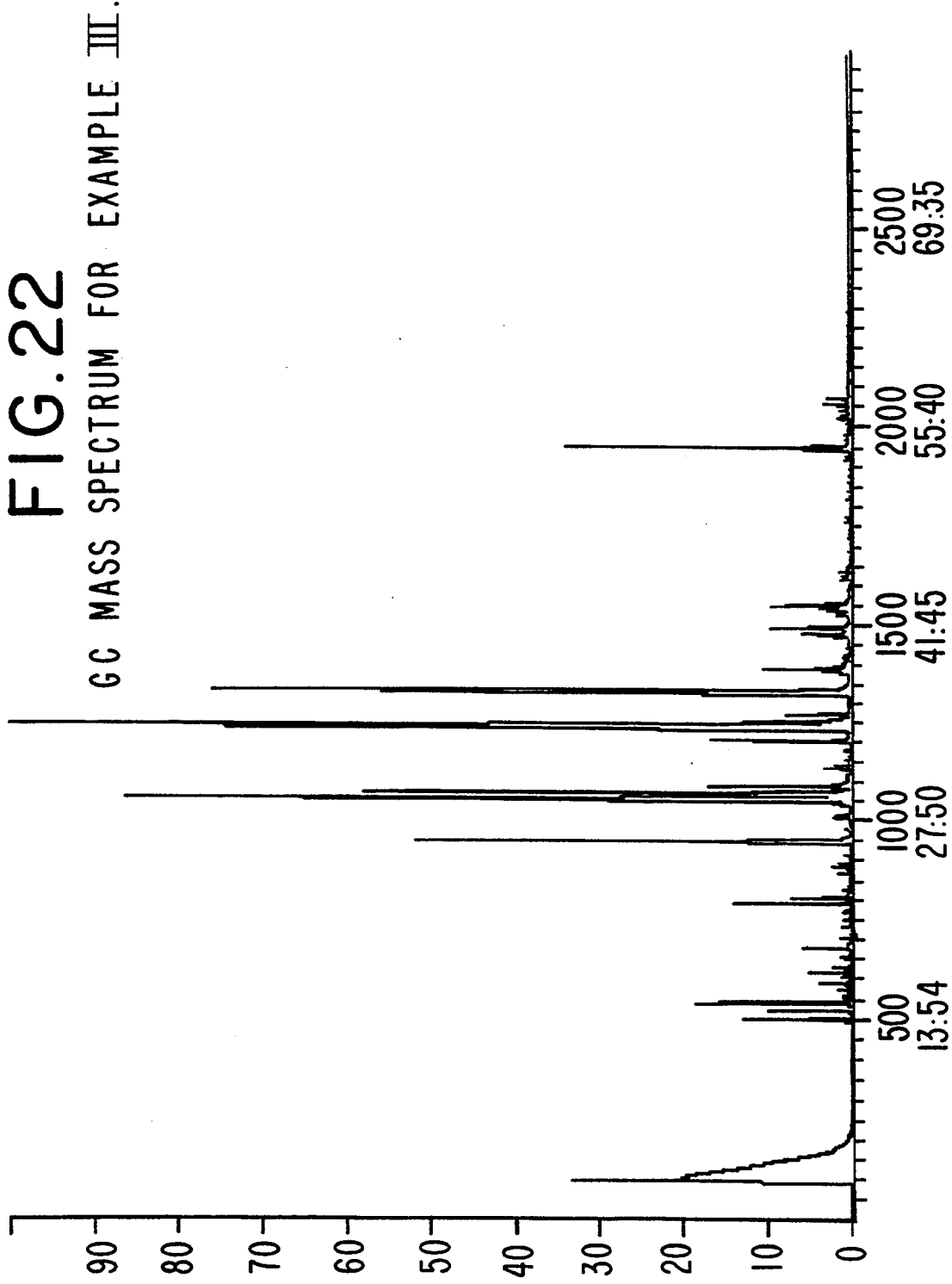
FIG. 22 is the GC-mass spectrum of the composition evolved from the two living flowers; Purple Heliotroprium Iowa and Jasminum Odoratissimum Flower using the apparatus of FIG. 1 in accordance with the procedure of Example III.

The analysis of the resulting headspace is set forth in the GC-mass spectrum of FIG. 21.

As a result of the foregoing analysis the major components of this analysis were obtained and formulated into a fragrance. These major components are as follows:

| Ingredients | Parts by Weight |
| --- | --- |
| 3-Methyl butyronitrile | 4.64 |
| 2-Pentenal | 1.05 |
| Pentanal oxime | 1.10 |
| 2,5-Dihydro-3-methyl furan | 8.64 |
| Myrcene | 9.16 |
| Limonene | 8.42 |
| Cis-Ocimene | 3.10 |
| Trans-ocimene | 1.18 |
| Methyl benzoate | 7.64 |
| 4,8-Dimethyl-1,3,7-nonatriene | 1.05 |
| 3,5-Dimethoxy toluene | 0.50 |
| Cis-jasmone | 0.65 |
| Germacrene-D | 0.65 |
| Alpha-farnesene | 8.42 |
| 1-Nonadecene | 1.05 |

The resulting fragrance can be described as "floral having rose, ginger and lily topnotes and rose, ginger and lily undertones".

EXAMPLE III

Analysis and Fragrance Preparation Using as the "Biflower", the Red Rose All That Jazz and the White Ginger Lily Flower A procedure was carried out identical to that of Example I with the exception that the two flowers contained in the headspace of the totally enclosed 3-space are the (i) red rose all that jazz and (ii) the white ginger lily flower.

The analysis of the resulting headspace is set forth in the GC-mass spectrum of FIG. 21.

As a result of the foregoing analysis the major components of this analysis were obtained and formulated into a fragrance. These major components are as follows:

| Ingredients | Parts by Weight |
|---|---|
| Cis-3-hexenol | 1.25 |
| Trans-2-hexenol | 1.35 |
| Benzaldeyde | 2.14 |
| Cis-3-hexenyl acetate | 7.25 |
| Trans-2-hexenyl acetate | 8.35 |
| Benzyl alcohol | 6.25 |
| Methyl benzoate | 1.56 |
| Linalool | 4.12 |
| Benzyl cyanide | 1.05 |
| Benzyl acetate | 0.54 |
| Methyl salicylate | 3.15 |
| Anisaldehyde | 0.52 |
| Beta-phenylethyl acetate | 1.51 |
| Indole | 0.64 |
| Alpha-farnesene | 4.12 |

The resulting fragrance can be described as "floral having rose, ginger and lily topnotes and rose, ginger and lily undertones".

EXAMPLE IV

Headspace Analysis and Perfume Formulation Resulting Therefrom Using Ginger Lily Flower and Jasminum Odoratissimum Flower A procedure was carried out identical to that of Example In the apparatus of FIG. 1 with the exception that the two flowers used in the apparatus are ginger lily flower and jasminum odoratissimum flower.

Figure 23:
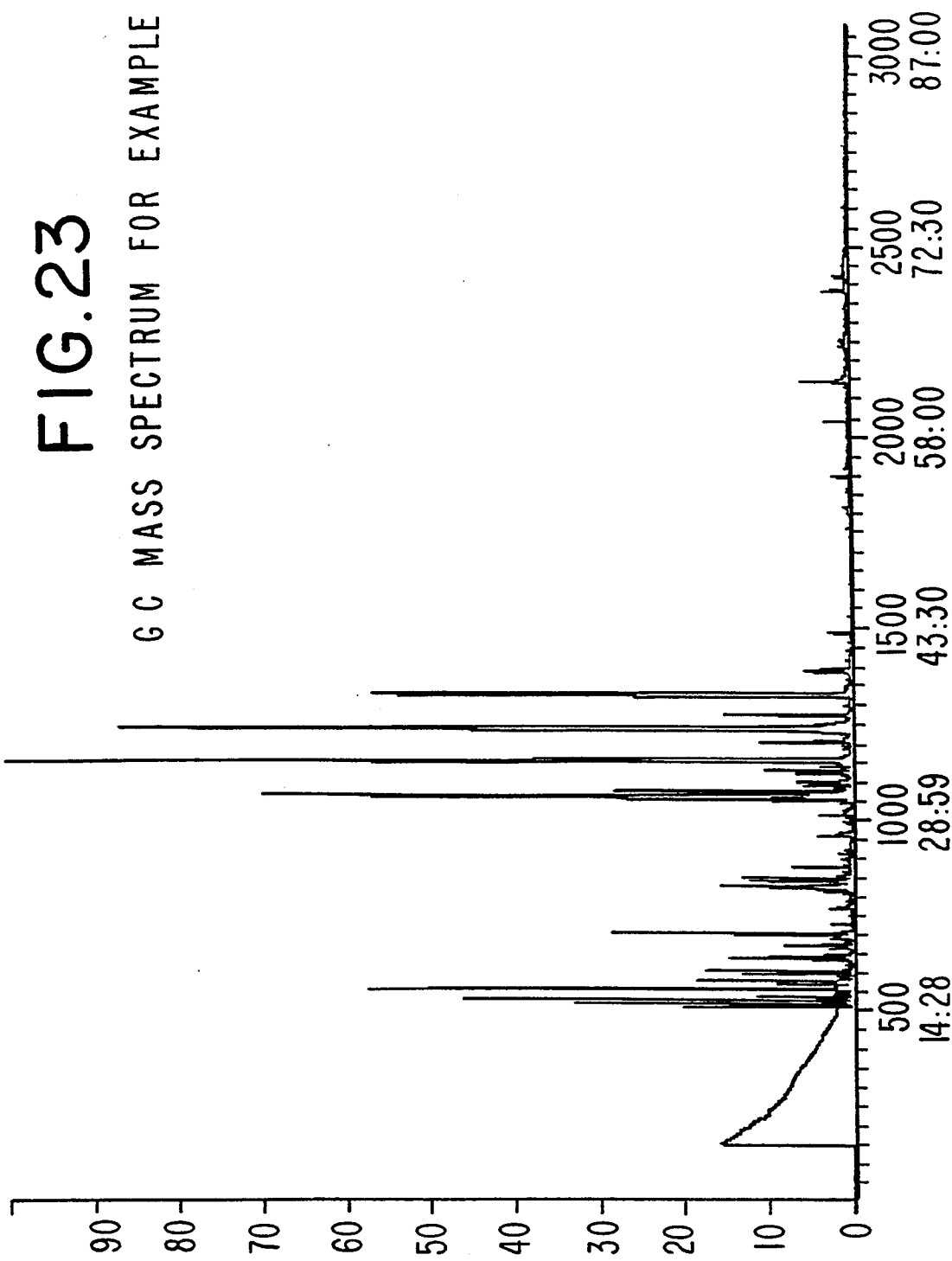
FIG. 23 is the GC-mass spectrum of the composition evolved from the two living flowers; the Ginger Lily Flower and the Jasminum Odoratissimum Flower using the apparatus of FIG. 1 in accordance with the procedure of Example IV.

The GC-mass spectral analysis is set forth in FIG. 23.

A perfume formulation was prepared containing the major components of the analysis, to wit:

| Ingredients | Parts by Weight |
|---|---|
| Cis-3-hexenyl acetate | 12.12 |
| Trans-2-hexenyl acetate | 4.11 |
| Linalool | 8.14 |
| Trans-beta-ocimene | 2.10 |
| Benzyl acetate | 4.22 |
| Beta-phenylethyl acetate | 6.81 |
| Methyl salycilate | 4.10 |
| Germacrene D | 0.52 |

The resulting formulation can be described as "floral with ginger and jasmine topnotes and ginger and jasmine undertones".

EXAMPLE V

Preparation of a Soap Composition

100 Grams of soap chips are admixed with 1 gram of one of the perfume substances of Table I below until a substantially homogeneous composition is obtained. The perfumed soap manifests an excellent aroma as set forth in Table I below:

TABLE I

| Perfume Ingredients | Aroma |
|---|---|
| Perfume composition of Example I. | A floral aroma with orange flower and green topnotes and green and jasmine undertones. |
| Perfume composition of Example II. | A floral aroma having rose, ginger and lily topnotes and rose, ginger and lily undertones. |
| Perfume composition of Example III. | A floral aroma having sweet, green, lilac and Hawthorne topnotes and fruity and jasmine undertones. |
| Perfume composition of Example IV. | A floral aroma with ginger and jasmine topnotes and ginger and jasmine undertones. |

TABLE I-continued

EXAMPLE VI

Preparation of a Cologne and Handkerchief Perfume

One of the perfume substances are set forth in Table I of Example V is incorporated into a cologne an concentrations of 1.5% 2.0% 2.5% 3.0% 3.5% and 4.0% in 80%, 85%, 90% and 95% aqueous ethanol and into handkerchief perfumes at concentrations of 15%, 20%, 25% and 30% (in 85%, 90% and 95% aqueous ethanol). Distinct and definite fragrances as set forth Table I of Example V are imparted to the cologne and to the handkerchief perfume at each of the levels Indicated.

EXAMPLE VII

Preparation of a Cosmetic Powder Composition

A cosmetic powder is prepared by mixing in a ball mill, 100 rams of talcum powder with 0.15 grams of one of the substances Table I of Example V. The resulting powders have excellent aromas as set forth in Table I of Example V.

EXAMPLE VIII

Utilizing the procedure of Example I of Column 15 U.S. Pat. No. 3,632,396 the specification for which is incorporated by reference herein, a non-woven cloth substrate useful as a drier-added fabric-softening article of manufacture is prepared wherein the substrate, the substrate coating and the outer coating and the perfuming material are as follows:

1. a water "dissolvable" paper ("Dissolvo paper");
2. Adogen 448 (m.p. about 140° F.) as the substrate coating; and
3. an outer coating having the following formulation (m.p. about 1.50° F.):
   57 percent—$C_{20-22}$HAPS
   27 percent—isopropyl alcohol
   20 percent—antistatic agent
   1 percent—of one of the perfume substances of Table I of Example V.

Fabric-softening compositions prepared as sen forth above having an aroma characteristic as set forth in Table I of Example V essentially consists of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and an outer coating weight ratio of about 1:1 by weight of the substrate. Aromas are imparted as set forth in Table I of Example V in a pleasant manner to the headspace in the dryer on operation thereof using the said dryer added fabric softening non-woven fabric.

EXAMPLE IX

Preparation of a Soap Composition

100 Grams of soap chips are prepared according to Example V of U.S. Pat. No. 4,058,490 issued on Nov.

15, 1977 the specification for which is incorporated herein by reference, as follows:

"The sodium salt of an equal mixture of $C_{10}$-$C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small about of a 50% aqueous solution of NaOH. The isopropanol is distilled off and the remaining aqueous solution is dried. The resulting solid actives are then blended in a chip mixer with 10 lbs. water 0.2 lb. titanium hydroxide."

The resulting blend is then mixed with one of the perfume substances of Table I of Example V until a substantially homogeneous composition is obtained. The perfumed soap composition manifests an aroma as set for the Table I of Example V.

EXAMPLE X

GRANULAR DETERGENT COMPOSITION

A granular detergent composition is prepared according to United Kingdom Patent No. 1,501,498 the specification for which is incorporated by reference herein having the following formula. It is prepared by spray-drying the following mixture:

| Ingredient | Parts by Weight |
| --- | --- |
| Sodium salt of ethoxylated fatty alcohol sulfate having an average of about 2.25 moles of ethylene oxide per mole of fatty alcohol | 14.1 |
| Sodium tallow alkyl sulfate | 2.4 |
| Sodium silicate solids ratio $SiO_2/Na_2O = 2.0$ | 6.0 |
| Sodium tripolyphosphate | 24.0 |
| $Na_{12}(AlO_2SiO_2)27H_2O$ | 18.0 |
| Moisture | 10.0 |
| Sodium sulfate | 25.0 |
| Perfume substance of Table I of Example V | 4.0 |

Laundry solutions containing the above detergent compositions are used to launder fabrics. Each of the laundry compositions both prior to and on laundering give rise to a pleasant aroma as set forth in Table I of Example V.

EXAMPLE XI

Perfumed Liquid Detergent

Concentrated liquid detergents are prepared with aromas as set forth in Table I of Example V containing 0.10%, 0.15% and 0.20% of each of the substances of Table I of Example V in the liquid detergent. The liquid detergent is a builder free liquid detergent consisting of (a) 50% of a nonionic surfactant having a HBL of 8.0 and a critical micelle concentration 0.007 weight percent at 25° C.; (b) an anionic surfactant which is a triethanolamine prepared according to United Kingdom Patent No. 1,491,603 the specification for which is incorporated by reference herein.

The detergents all possess aromas as set forth in Table I of Example V, supra.

EXAMPLE XII

Preparation of a Detergent Composition

A total of 100 grams of detergent powder (a low phosphate content detergent composition which contains 12% by weight phosphate builder, 8 percent hardness mineral ion insensitive detergent, 0.9 percent by weight maleic anhydride-vinyl compound co-polymer and 2 percent alkylene oxide condensation product prepared according to Example IV at column 9, U.S. Pat. No. 4,000,080 issued on Dec. 28, 1976, the specification for which is incorporated by reference herein) is intimately admixed with 0.15 grams of one of the perfume materials of Table I of Example V, supra, until a substantially homogeneous composition is obtained. The composition has an aroma as set forth in Table I of Example V, supra.

EXAMPLE XIII

Each of the fragranced material of Table I of Example V, supra, are added to a 50:50 weight:weight mixture of low density polyethylene:polyepsilon caprolactone PCL-700 forming pellets with scents as set forth in Table I of Example V supra.

75 Pounds of a mixture of PCL-700 polyepsilon caprolactone (manufactured by the Union Carbide Corporation of New York, New York having a melting point of about 180°-190° F.): low density polyethylene are heated to about 250° C., in a container of the kind illustrated in FIGS. 24 and 25. 25 Pounds of each of the fragrance materials as set forth in Table I of Example V is then quickly added to the liquified polymer mixture, the lid 228 is put in place and the agitating means 273 are actuated. The temperature is then raised to about 260° F. and the mixing continued for 5-15 minutes. The valve "V" is then opened to allow flow of the molten polymer enriched with perfume ingredient to exit through the orifices 234. The liquid falling through the orifices 234 solidified almost instantaneously upon impact with the moving cooled conveyor 238. Polymer beads or pellets 244 having pronounced scents as described in Table I of Example V, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table I of Example V, supra. The sheets of films are cut into strips of 0.25" in width×3" in length and placed into room air fresheners.

On operation of the room air freshener, after four minutes the room in each case has an aesthetically pleasing aroma with no foul odor being present, the aroma being described in Table I of Example V, supra.

EXAMPLE XIV

Each of the LIVING FLOWER ® perfume compositions of Table I of Example V are individually admixed with CLARYCET ™ (trademark of International Flavors & Fragrances Inc. for the ester having the structure:

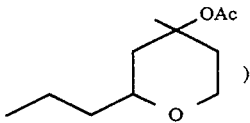

in the ratio of 10 parts by weight of ester to one part by weight of LIVING FLOWER® perfume composition. At the rates of:

100 ppm;
150 ppm; and
200 ppm the resulting composition is added to EXXON® middle distillate fuel heating oil in accordance with the procedure of European Published Application 532556 published on Mar. 24, 1990 (corresponding to PCT Application 91/18961-A).

On use, in each case, the unpleasant "burnt fuel oil" nuances are completed masked and "faint pleasant aromas" described in Table I of Example V are imparted to the environments surrounding the burning heating oil.

What is claimed is:

1. A process for qualitatively and quantitatively analyzing the aroma emitted and rates of emission of the aroma components thereof from two or more different varieties and/or species of living flowers, living leaves, living trees and/or living fruits at a given point in time over a given time period using separate enclosures, one or more of which each contains one or more living flowers and/or one or more living leaves and/or one or more living fruits and/or one or more of which separately covers a portion of the outer surface of the bark of a living tree and/or one or more of which separately converts a portion of the outer surface of a living fruit, and having a single aroma trapping means communicating in manifold fashion with all of the single enclosures comprising the steps of:

(a) providing at least two hollow enclosures each of which has (i) an outer wall containing at least two outer wall orifices including a first wall orifice and a second wall orifice and (ii) an inner three dimension space providing for the separate individual unobstructed maintenance of at least one single living fruit and/or living leaf and/or living flower or a portion of the outer surface of a living fruit or a portion of the outer surface of the bark of a living tree;

(b) causing the insertion of at least one living fruit variety or species or a living leaf variety or species or a living flower variety or species separately through each orifice of each hollow enclosure or causing one or more of said hollow enclosures to be sealably affixed at one of its orifices to a portion of the surface of the bark of a living tree or to a portion of the surface of a living fruit;

(c) causing an orifice of each of said hollow enclosures to be engaged with and juxtaposed to a substantially cylindrical feeding tube having an outer feeding tube end having a substantially circular rim tightly fitted at its rim into said orifice of said enclosure and a lower feeding tube end having a substantially circular rim jointly and sealably affixed at its rim and communicating with a common hollow totally enclosed volumetric mixing junction to the upper rim of the upper opening of a substantially cylindrical key tube, said key tube being a hollow substantially cylindrical tube having an internal key tube diameter and a Key tube length and having an upper key tube opening having an upper substantially circular key tube rim and a lower key tube opening having a lower substantially circular key tube rim with a trapping cylinder contained (i) partially within said key the and (ii) extending beyond said lower key tube opening, said trapping cylinder being substantially concentric with said key tube, said trapping cylinder consisting of a hollow cylindrical tube containing a trapping material for trapping volatiles, having an outer trapping tube diameter substantially less than the inner key tube diameter, the space between the key tube and the trapping cylinder being sealed in gas-tight fashion;

(d) causing a vacuum pumping means to be juxtaposed with, and engaging said lower end of said trapping tube means whereby said vacuum pumping means exerts a negative pressure on each of said enclosed three dimensional spaces whereby all of said aroma components are transmitted from each of said three dimensional spaces of said hollow enclosures into said trapping tube;

(e) removing the trapping material from the trapping tube;

(f) extracting the aroma components from the trapping material; and (g) carrying out a qualitative and quantitative analysis of said aroma components.

2. An analytical volatile substance trapping apparatus subcombination comprising:

(x) a hollow substantially cylindrical key tube having an internal key tube diameter and a key tube length; and having an upper key tube opening having an upper substantially circular rim and a lower key tube opening having a lower substantially circular ri;

(y) a trapping cylinder contained partially within said key tube, extending substantially beyond said lower key tube opening and substantially concentric with said key tube, said trapping cylinder consisting of a hollow cylindrical tube containing trapping material for trapping volatiles; said trapping cylinder having an outer trapping tube diameter substantially less than the inner diameter of said tube, the space between the key tube and the trapping cylinder being sealed in gas-tight fashion; and (z) communicating with, and jointly and sealably affixed at a common hollow totally enclosed volumetric mixing junction to the said upper rim of said upper opening of said key tube, a plurality of hollow substantially cylindrical feeding tubes extending in diverse directions away from said key tube upper rim, each of said feeding tubes having an outer substantially circular feeding tube rim, and a lower substantially circular feeding tube rim, said lower feeding tube rim being sealably affixed and communicating with said volumetric mixing junction, such that a continuous unbroken travel path for molecules of volatiles exists from each of said outer feeding tube rims to the said lower rim of said trapping cylinder, whereby volatiles pass through said feeding tubes in a direction towards said key tube and are entrapped in said trapping material located in said trapping tube.

3. Apparatus for qualitatively and quantitatively analyzing the aroma emitted and rates of emission of the aroma components thereof from two or more different varieties and/or species of living leaves, living flowers, living trees and/or living fruits at a given point in time or over a given period of time using separate enclosures, one or more of which each contains at least one single living flower and/or at least one single living fruit and/or at least one single living leaf and/or one or more of which separately covers a portion of the outer surface of the bark of a living tree and/or one or ore of which covers a portion of the outer surface of a living fruit and having a single aroma trapping means communicating in manifold fashion with all of the single enclosures comprising:

(a) two or more hollow enclosures each of which has (i) an outer wall containing at least two outer wall orifices spaced at a finite distance from one another including a first outer wall orifice and a outer wall orifice and (ii) an inner 3-dimensional space providing for the separate maintenance of at least one single living fruit and/or a living leaf and/or a living flower or a portion of the outer surface of the bark of a living tree or a portion of the outer surface of a living fruit;

(b) having inserted into at least one orifice of each of said hollow enclosures at least one living fruit variety or species and/or at least one living leaf variety or species and/or at least one living flower variety or species and/or causing one or more of said hollow enclosures to cover at an orifice of said hollow enclosure a portion of the outer surface of a living fruit and/or at an orifice of said hollow enclosure a portion of the outer surface of the bark of a living tree;

(c) communicating with and juxtaposed to an orifice of each of said hollow enclosures, a single substantially cylindrical feeding tube each of which feeding has a lower end having a substantially circular lower rim and an outer substantially circular feeding tube end having a substantially circular outer rim, sealably affixed to said orifice of said enclosure;

(d) each of said feeding tubes at said lower rim being jointly and sealably communicative and affixed at a common hollow totally enclosed volumetric mixing junction to the upper rim of the upper opening of a single key tube, the key tube being a hollow substantially cylindrical key tube having an internal key tube diameter and a key tube length and having upper key tube opening having an upper substantially circular rim and a lower key tube opening having a lower substantially circular rim with;

(e) a trapping cylinder contained partially within said key tube and substantially concentric with said key tube, said trapping cylinder extending beyond said lower key tube opening, said trapping cylinder consisting of a hollow cylindrical tube containing trapping material for trapping volatiles emitted from said one or more living leaves and/or said one or more living fruits and/or said one or more living flowers and/or said one or more surface portions of said living fruits and/or said one or more bark surface portions of said living trees, said trapping tube having a trapping tube diameter substantially less than said key tube diameter; and (f) juxtaposed with and engaging said lower end of said trapping tube a vacuum pumping means exerting a negative pressure on said enclosed 3-space whereby said aroma components are transmitted from said 3-space into said trapping tube means and onto said trapping material.

4. The process of claim 1 including the additional of: (h) preparing a flavor or fragrance composition base on the analysis carried out in step (g).

5. The apparatus of claim 3 comprising in addition means for removing the aroma component-bearing trapping material from said trapping tube means; (h) extraction means for extracting the aroma components from the aroma component-bearing trapping material thereby forming an extracted aroma component composition; and (j) analysis means for carrying out qualitative and quantitative analysis on the extracted aroma component composition.

6. The apparatus of claim 3 wherein infrared and/or ultraviolet radiation means impinges infrared and/or ultraviolet radiation on one or more of said enclosures.

7. The process of claim 1 wherein two separate hollow enclosures each containing single living flower species are provided.

8. The apparatus of claim 3 which comprises two separate hollow enclosures containing separate individual living flower species.

9. The apparatus of claim 5 which comprises two separate hollow enclosures containing separate individual living flower species.

10. The process of claim 4 wherein two separate hollow enclosures each containing single living flower species are provided.

11. The apparatus of claim 8 wherein infrared and/or ultraviolet radiation means impinges infrared and/or ultraviolet radiation on one or more of said enclosures.

12. The process of claim 1 having the additional steps of:

(h) procuring from an independent source at least the major aroma components determined according to step (g); and (k) admixing the aroma components procured in step (h) thereby forming a perfume composition.

13. A process for forming a perfumed polymer comprising the step of intimately admixing a thermoplastic polymer in the liquid or solid phase with an aroma imparting quantity of a fragrance composition prepared according to claim 12.

14. A process for forming a perfumed article comprising the step of intimately admixing with a perfumed article base an aroma augmenting, enhancing or imparting quantity of a perfume composition defined according to claim 12.

15. A process for forming a cologne comprising the step of intimately admixing water, ethanol and an aroma imparting quantity of a perfume composition defined according to claim 12.

* * * * *